(12) United States Patent
Nishiuchi et al.

(10) Patent No.: US 8,372,105 B2
(45) Date of Patent: Feb. 12, 2013

(54) PUNCTURE INSTRUMENT

(75) Inventors: Daisuke Nishiuchi, Nakakoma-gun (JP); Takayuki Sugiyama, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 323 days.

(21) Appl. No.: 12/673,281

(22) PCT Filed: Aug. 22, 2008

(86) PCT No.: PCT/JP2008/065468
§ 371 (c)(1),
(2), (4) Date: Feb. 12, 2010

(87) PCT Pub. No.: WO2009/025395
PCT Pub. Date: Feb. 26, 2009

(65) Prior Publication Data
US 2011/0137203 A1 Jun. 9, 2011

(30) Foreign Application Priority Data
Aug. 23, 2007 (JP) .................................. 2007-216807
Feb. 19, 2008 (JP) .................................. 2008-037631

(51) Int. Cl.
*A61B 17/14* (2006.01)
*A61B 17/32* (2006.01)
(52) U.S. Cl. .......................... 606/181; 606/182; 606/185
(58) Field of Classification Search .................. 606/181, 606/182, 185, 167, 183, 184; 600/583; 604/22, 604/110, 117, 207, 208, 210
See application file for complete search history.

(56) References Cited

U.S. PATENT DOCUMENTS
4,892,097 A 1/1990 Ranalletta et al.
(Continued)

FOREIGN PATENT DOCUMENTS
JP 2005-230570 A 9/2005
JP 3795511 B2 4/2006
(Continued)

OTHER PUBLICATIONS
International Search Report issued by the Japanese Patent Office on Nov. 21, 2008 as the International Searching Authority in International Application No. PCT/JP2008/065468.
(Continued)

*Primary Examiner* — Ryan Severson
*Assistant Examiner* — Tin Nguyen
(74) *Attorney, Agent, or Firm* — Buchanan Ingersoll & Rooney PC

(57) ABSTRACT

A puncture instrument includes a needle assembly, a hub passage for axially guiding a hub, a needle passage communicating with the hub passage and having a distal end opening for allowing the tip end of a needle to project instantaneously therethrough, two arms having first junctions connected to the hub and inclined rearward in a direction away from the hub in an initial state, two push rods connected to second junctions of the arms and extending rearward, a button for pushing the push rods forwardly, and fulcrum members disposed more closely to the distal end than the arms for abutment against portions of the arms when the arms are moved. When the push rods are pushed forwardly by the button, the arms push the needle assembly forwardly, thereafter have portions thereof brought into abutment against the fulcrum members, and turn to pull the needle assembly rearward.

20 Claims, 28 Drawing Sheets

U.S. PATENT DOCUMENTS 5,366,470 A * 11/1994 Ramel .......................... 606/183
5,527,334 A * 6/1996 Kanner et al. ................. 606/182

FOREIGN PATENT DOCUMENTS

WO    WO 2007/024152 A2    3/2007

OTHER PUBLICATIONS

Written Opinion issued by the Japanese Patent Office on Nov. 21, 2008 as the International Searching Authority in International Application No. PCT/JP2008/065468.

* cited by examiner

PUNCTURE INSTRUMENT

TECHNICAL FIELD

The present invention relates to a puncture instrument comprising a needle for instantaneously projecting the needle to puncture the human skin therewith.

BACKGROUND ART

Diabetic patients are generally recommended to perform a daily self-management of diabetes by measuring blood sugar levels by themselves. Blood sugar levels can be measured using blood component measuring devices. According to one blood component measuring device, it holds a test paper impregnated with a reagent which produces a color change dependent on the amount of glucose contained in a blood sample that is brought into contact with the test paper. In operation, a blood sample is applied to the test paper, and the degree of a color change produced by the reagent is optically measured to determine the blood sugar level of the blood sample. The determined blood sugar level is then displayed. Another blood component measuring device employs an electrochemical sensor for measuring the blood sugar level of a blood sample.

In order for a diabetic patient to sample its own blood, the diabetic patient uses a puncture instrument equipped with a puncture needle tip having an axially movable needle. The puncture needle tip, which is removably mounted on the puncture instrument, exerts repulsive force from an elastic body to a needle therein to cause the needle to project instantaneously and puncture the skin, e.g., a finger, a palm, an arm, or the like, of the patient for thereby letting a small amount of blood to flow out. After the puncture, the needle is retracted by a return mechanism.

Generally, the puncture instrument is used with the puncture needle tip mounted thereon, and the puncture needle tip is thrown away after use. Though hospitals and clinics have a considerably large number of puncture needle tips ready for use depending on the number of patients and the frequency of blood sugar measurements, they have a relatively small number of puncture instruments available. Therefore, if many patients need to be simultaneously measured for blood sugar levels, it may take a longer time to measure blood sugar levels for all the patients than usual because not enough puncture instruments may be available. Since a puncture needle tip has to be mounted on and removed from the puncture instrument for each measurement session, there are demands for simpler puncture instruments.

Japanese Patent No. 3795511 discloses a simple lancet assembly integrally combined with a puncture needle tip. The disclosed lancet assembly makes it unnecessary to mount and remove the puncture needle tip each time a blood sample is to be obtained.

DISCLOSURE OF INVENTION

It is an object of the present invention to provide a puncture instrument which can be operated stably and is simple in structure.

A puncture instrument according to the present invention comprises a case, a needle assembly movably disposed in the case and including a needle and a hub holding the needle, a hub passage for axially guiding the hub, the hub passage being disposed in the case, a needle passage disposed in the case and communicating with the hub passage, the needle passage having a distal end opening for allowing a tip end of the needle to project therethrough, at least one arm having a first junction on an end thereof connected to the hub and a second junction on another end thereof, the arm being inclined from the first junction toward a proximal end of the case in an initial state, a push rod joined to the second junction and extending toward the proximal end, a pusher for pushing the push rod toward a distal end of the case, and a fulcrum member for abutting against a portion of the arm when the arm moves, wherein when the push rod is pushed toward the distal end by the pusher, the arm pushes the needle assembly toward the distal end, brings the portion thereof into abutment against the fulcrum member, and turns about the fulcrum member, so that the arm is inclined from the first junction toward the distal end thereby to pull back the needle assembly toward the proximal end.

With the above puncture instrument, the needle assembly is pushed directly by the push rod, is not mediated with an elastic body for axially biasing the needle assembly, can puncture a skin stably, and is simple in structure. After the needle has punctured the skin, the arm turns about the fulcrum member to pull back the needle reliably out of the skin. The term "case" referred to above is used in a broad sense and represents a member serving as a base of the puncture instrument.

The push rod may comprise a leaf spring which is elastically deformable under the force applied from the arm when the push rod is pushed toward the distal end by the pusher. If the push rod comprises a leaf spring, then it does not obstruct the turning of the arm and allows the arm to operate more stably. When the needle assembly has finished its movement, the needle assembly is resiliently biased to move rearward under the resilient force of the push rod.

The arm may be inclined toward the proximal end in a direction away from the hub in the initial state, and when the push rod is pushed toward the distal end as the pusher is pushed, the arm may turn about the fulcrum member and incline toward the distal end in a direction away from the hub.

At least one of the first junction and the second junction may be narrower than the arm and may be plastically deformable when the arm turns and changes its inclination direction. If at least one of the first junction and the second junction is plastically deformable, then the pusher is stably kept in a stroke end position and does not move back to the initial state. Thus, the puncture instrument is prevented from being reused.

The hub may include a base on a proximal end portion thereof and having a flat surface parallel to a plane in which the arm turns, the first junction being rotatably connected to the base at a position on the plane which is spaced a predetermined distance from a longitudinal axis of the hub.

The pusher may include a convex or concave engaging portion, and the case may include a first engageable portion for engaging the engaging portion when the pusher is in an initial position, and a second engageable portion for engaging the engaging portion when the pusher is in a stroke end position.

In the initial position, the pusher has its engaging portion engaging the first engageable portion and will not move accidentally. When the pusher is strongly pushed toward the distal end, the engaging portion disengages from the first engageable portion, allowing the pusher and the needle assembly to move forcefully toward the distal end. The needle can thus puncture the skin at a certain speed. Thereafter, the engaging portion engages the second engageable portion, holding the pusher stably in position.

The pusher may be movably disposed in an inner cavity formed in the case and have a proximal end projecting from the case by a distance ranging from 5 to 30 mm when the pusher is in an initial position, and projecting from the case by a distance of less than 5 mm when the pusher is in a stroke end position. With this arrangement, the user of the puncture instrument can easily recognize whether the puncture instrument has been used or not by confirming the position of the pusher projecting from the case. After the puncture instrument has been used, the pusher is inserted almost entirely in the case and prevented from being accidentally pulled back out of the case.

The needle passage may be narrower than the hub passage, and a step is provided between the needle passage and the hub passage, for abutting a distal end surface of the hub on the step to limit the needle assembly against movement. The step is reliably effective to limit the needle assembly against movement, thereby achieving an appropriate depth to which the needle punctures the skin.

The arm may comprise two arms and the push rod may comprise two push rods, the two arms and the two push rods being symmetrical about a longitudinal axis of the hub. The two arms and the two push rods provide a relatively simple structure with few components, are symmetrical in structure, and are well balanced.

The puncture instrument may further comprise biasing means for biasing the pusher to be pushed toward the distal end, and a stopper for limiting the pusher biased by the biasing means against movement toward the distal end and releasing the pusher in response to operation of a trigger. The biasing means allows the user to operate the trigger with light force to cause the needle to puncture the skin.

The case may be of a hollow cylindrical shape, and the puncture instrument may further comprise a protective cap removably mounted on a distal end of the case for holding and sealing the needle in the needle passage. The hollow cylindrical case can highly be sealed when the protective cap is mounted thereon, thereby keeping the needle sterilized.

The puncture instrument according to the present invention offers the following advantages.

The needle assembly is pushed directly by the push rod, is not mediated with an elastic member for axially biasing the needle assembly, can puncture a skin stably, and is simple in structure. After the needle has punctured the skin, the arm turns about the fulcrum member to pull back the needle reliably out of the skin.

Further, the lancet assembly disclosed in Japanese Patent No. 3795511 looks as if it performs puncture with a single operation. Inside the lancet assembly, however, a spring needs to be compressed just before puncture, and then the puncture is triggered. If the spring is compressed well in advance, the spring characteristics tend to be deteriorated. Although such a two-step operation can avoid the spring deterioration, the inside structure of the lancet assembly becomes complex. In contrast, because the puncture instrument of the present invention does not require a spring, the spring deterioration does not affect and a simple structure can be realized.

The above and other objects, features, and advantages of the present invention will become more apparent from the following description when taken in conjunction with the accompanying drawings in which preferred embodiments of the present invention are shown by way of illustrative example.

BEST MODE FOR CARRYING OUT THE INVENTION

Figure 1:
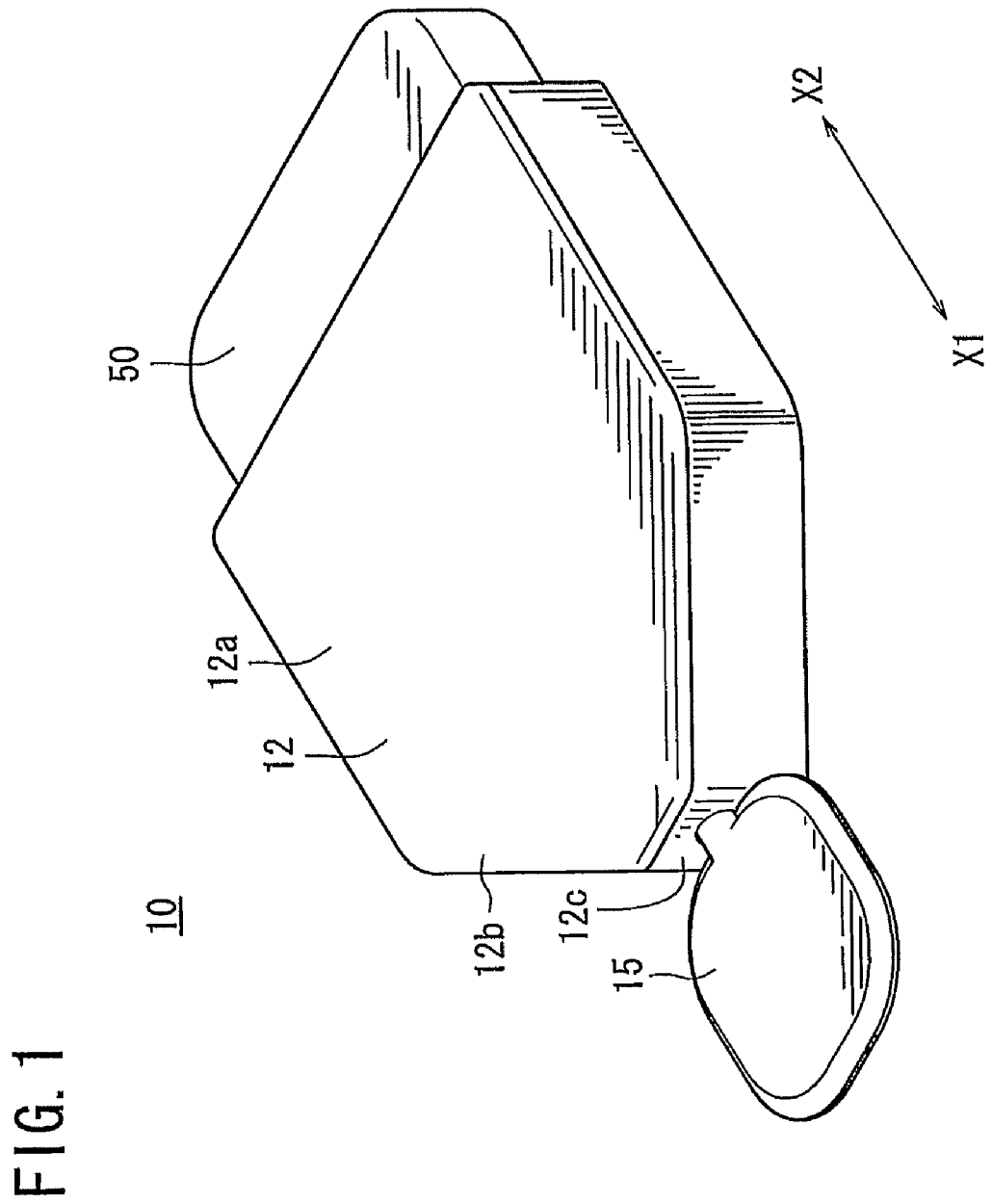
FIG. 1 is an external perspective view of a puncture instrument according to a first embodiment of the present invention.

Puncture devices according to preferred embodiments of the present invention will be described below with reference to FIGS. 1 to 28 of the accompanying drawings. The direction indicated by the arrow X1 in FIG. 1 points toward a front side (distal end) of the puncture instrument, and the direction indicated by the arrow X2 in FIG. 1 points toward a rear side (proximal end) of the puncture instrument.

As shown in FIGS. 1 to 9, a puncture instrument 10 according to a first embodiment of the present invention comprises a case 12, a movable member 14 movably disposed in the case 12, and a protective cap 15. The case 12 serves as a base of the puncture instrument 10 and has a thin body of pentagonal shape including a substantially square rear portion 12a and a tapered front portion 12b. The puncture instrument 10 can be made of resin (e.g., polypropylene or polyethylene) or metal except for a needle 40 to be described later. The case 12 has a distal end face 12c having a suitable area for abutting against the skin of a patient.

Figure 2:
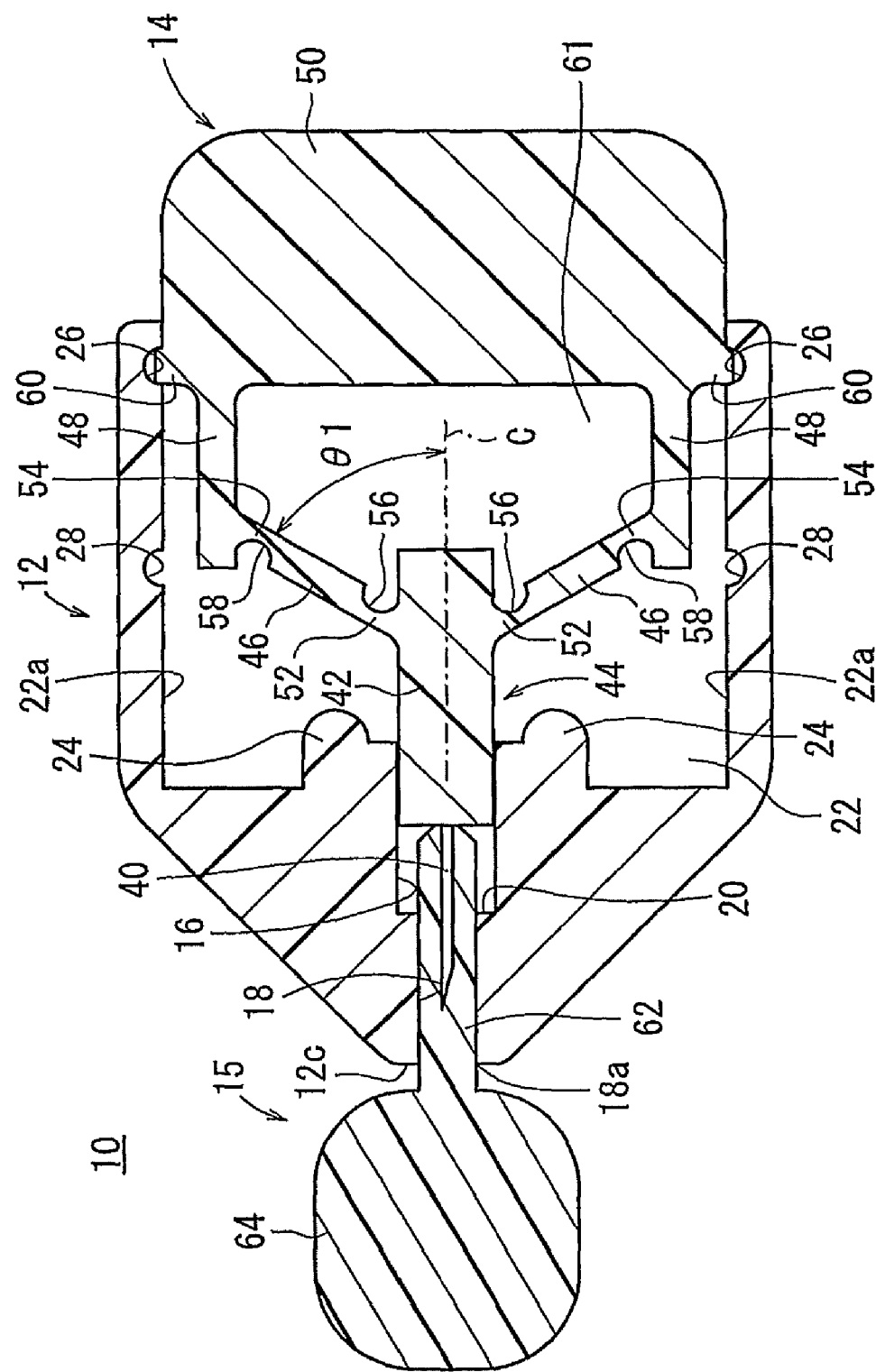
FIG. 2 is a cross-sectional view of the puncture instrument shown in FIG. 1, showing an initial state thereof.

As shown in FIG. 2, the front portion 12b has a hub passage 16 and a needle passage 18 which are formed axially therethrough. The needle passage 18 has a distal end opening 18a which is open at the distal end face 12c and a rear end communicating with the hub passage 16. The needle passage 18 is smaller in diameter than the hub passage 16, with a step 20 being disposed between the needle passage 18 and the hub passage 16.

The rear portion 12a has an inner cavity 22 formed by walls surrounding in four directions. The inner cavity 22 has a front central end communicating with the hub passage 16 and a rear end which is open rearward. The rear portion 12a has a front wall defining the front end of the inner cavity 22 and including two fulcrum members 24 slightly projecting rearward from respective portions in the front wall on the opposite sides of the hub passage 16. Each of the fulcrum members 24 has a rear end having a semicircular cross-sectional shape in the planar view.

The lateral walls 22a of the inner cavity 22 each includes a first recess (first engageable portion) 26 formed therein near the open rear end of the inner cavity 22 and a second recess (second engageable portion) 28 formed therein at substantially axially central position. The lateral walls 22a have flat smooth surfaces except the first recesses 26 and the second recesses 28.

Figure 3A:
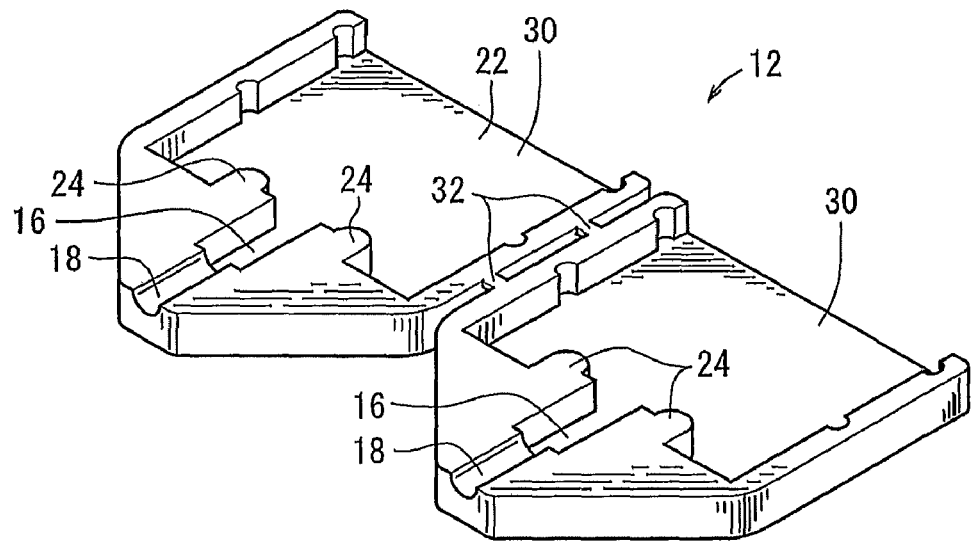
FIG. 3A is a perspective view of a case according to a first example as it is spread out.
Figure 3B:
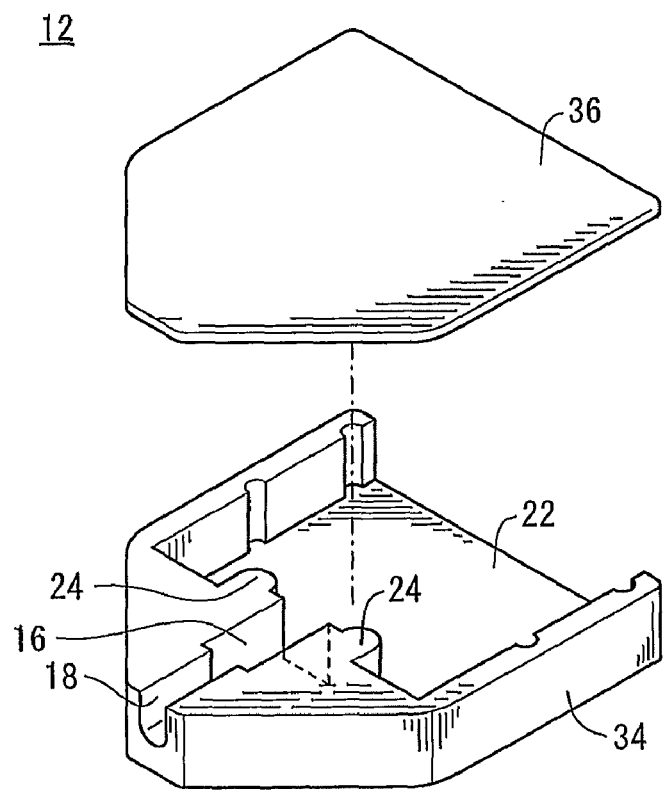
FIG. 3B is a perspective view of a case according to a second example.

As shown in FIG. 3A, according to a first example, the case 12 comprises two symmetrical members 30 joined to each other by short bendable members 32. The symmetrical members 30 can be brought together about the bendable members 32. As shown in FIG. 3B, according to a second example, the case 12 comprises a main body 34 including the hub passage 16, the needle passage 18, and the inner cavity 22, and a lid 36 placed over the main body 34. The main body 34 and the lid 36 may be joined to each other by members similar to the bendable members 32 shown in FIG. 3A.

Figure 4:
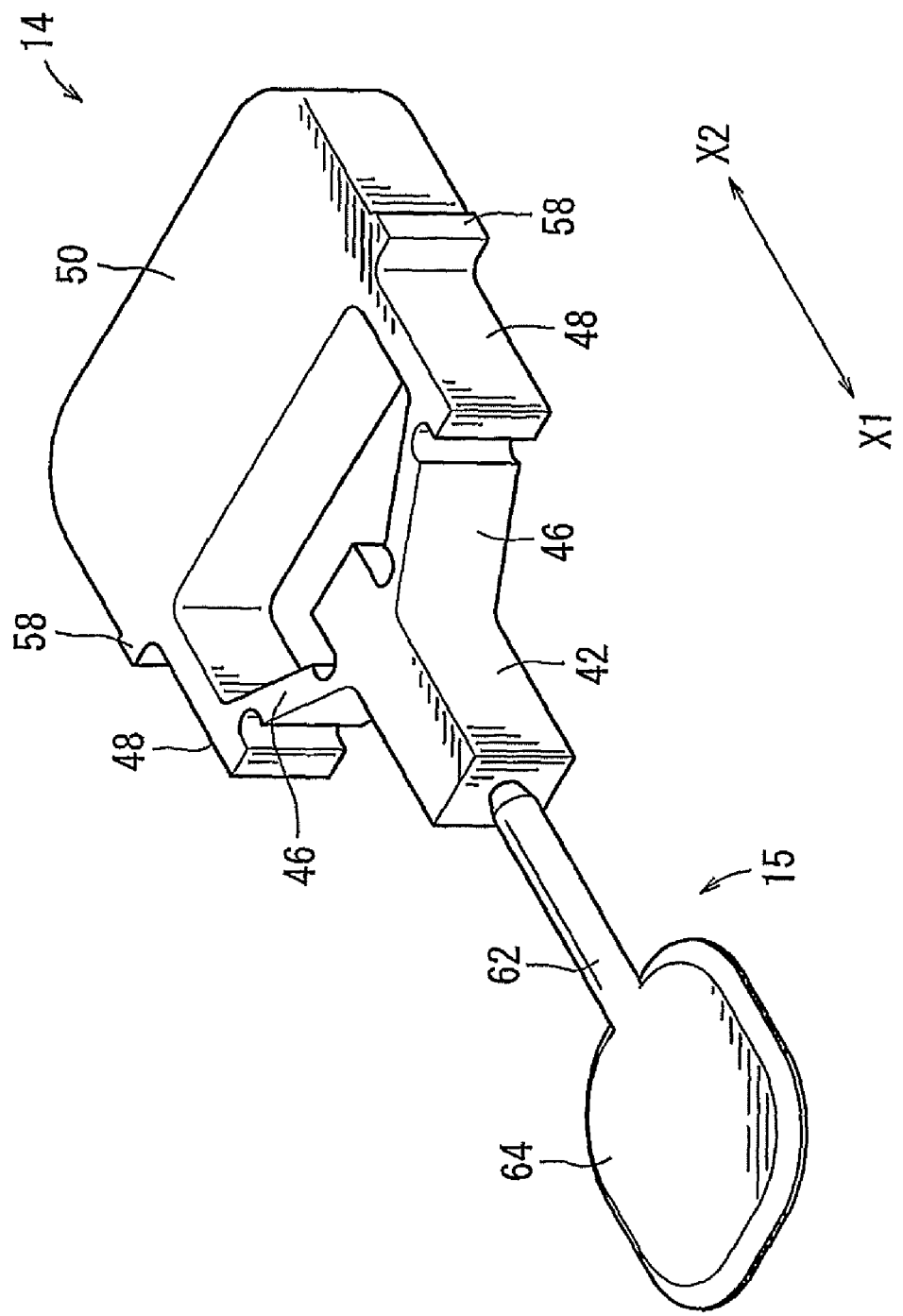
FIG. 4 is a perspective view of a movable member of the puncture instrument.

As shown in FIGS. 2 and 4, the movable member 14 comprises a needle assembly 44 including a needle 40 and a hub 42 holding the needle 40, a pair of arms 46 and a pair of push rods 48 which are symmetrically shaped with respect to the longitudinal axis C of the hub 42, and a pusher button (pusher) 50 for pushing the push rods 48 forwardly. Since the movable member 14 has the two arms 46 and the two push rods 48, the arms 46 and the push rods 48 are relatively small in number and simple in structure, and are well-balanced as they are symmetrical in shape. However, the movable member 14 may have a single arm 46 and a single push rod 48 or three or more arms 46 and three or more push rods 48. If the movable member 14 has three or more arms 46 and three or more push rods 48, then the arms 46 and the push rods 48 may be angularly equally spaced from each other around the longitudinal axis C of the hub 42.

The needle 40 comprises a hollow needle or a solid needle which is made of a metal such as stainless steel, aluminum, or titanium or a hard resin such as polyphenylene sulfide. The push rods 48 have a sufficient mechanical strength for pushing the arms 46 and the needle assembly 44 and are elastic enough to be bendable outwardly. The push rods 48 thus have a function as leaf springs. When the push rods 48 are in an initial state shown in FIG. 2, i.e., in storage prior to use, the push rods 48 are free of elastic strains and their resilient force will not be reduced even when the push rods 48 are kept in storage over a long period of time.

The needle 40 serves to puncture the skin of a patient and is disposed in a front portion of the needle assembly 44. In the initial state as shown in FIG. 2, the needle 40 has its tip inserted in the needle passage 18.

Each of the arms 46 includes a first junction 52 at one end connected to the hub 42 and a second junction 54 at the other end connected to the distal end of the push rod 48. In the initial state, the arms 46 are spread outwardly in the rearward direction, and are inclined rearward in respective directions away from the longitudinal axis C of the hub 42. The arms 46 are inclined to the longitudinal axis C of the hub 42 at an angle θ1 of about 50°, for example.

The arms 46 have respective recesses 56 formed in rear surfaces thereof at the first junctions 52, and respective recesses 58 formed in front surfaces thereof at the second junctions 54. Therefore, the first junctions 52 and the second junctions 54 are narrower than the rest of the arms 46.

The distal ends of the push rods 48 are joined to the respective arms 46. The push rods 48 extend rearward substantially parallel to the longitudinal axis C of the hub 42, and have respective rear ends joined to a front surface of the pusher button 50. The push rods 48 are appropriately spaced from the lateral walls 22a.

The pusher button 50 essentially closes the rear opening of the inner cavity 22. In the initial state, only a front end portion of the pusher button 50 is inserted in the inner cavity 22. The front end portion of the pusher button 50 which is inserted in the inner cavity 22 has a pair of protrusions (engaging portions) 60 on opposite outer sides thereof which engage in the respective first recesses 26 in the initial state. The pusher button 50 has a rear end projecting a certain distance from the case 12 and having arcuate corners which allow a human hand to operate the pusher button 50 with ease. The distance by which the rear end of the pusher button 50 projects from the case 12 is in the range from 5 to 30 mm, for allowing the human hand to push the pusher button 50 with ease.

The movable member 14 has a space 61 defined therein which is surrounded by the hub 42, the arms 46, the push rods 48, and the pusher button 50.

The protective cap 15 comprises a tubular member 62 inserted in the hub passage 16 and the needle passage 18 and covering the needle 40, and a tab 64 connected to the front end of the tubular member 62. The tubular member 62 has a tapered rear end fixed to the front end face of the hub 42 by fusion, adhesive bonding, or the like. The needle 40 has a needle tip portion sealed in the tubular member 62 by insert molding. The hub 42 and the protective cap 15 may be integrally molded. The protective cap 15 is irradiated with γ-rays, electron beams, or the like to sterilize the needle 40 in the tubular member 62.

Operation of the puncture instrument 10 thus constituted will be described below.

First, the tab 64 is twisted to wring the tubular member 62 off the hub 42, and the protective cap 15 is removed from the case 12.

Figure 5:
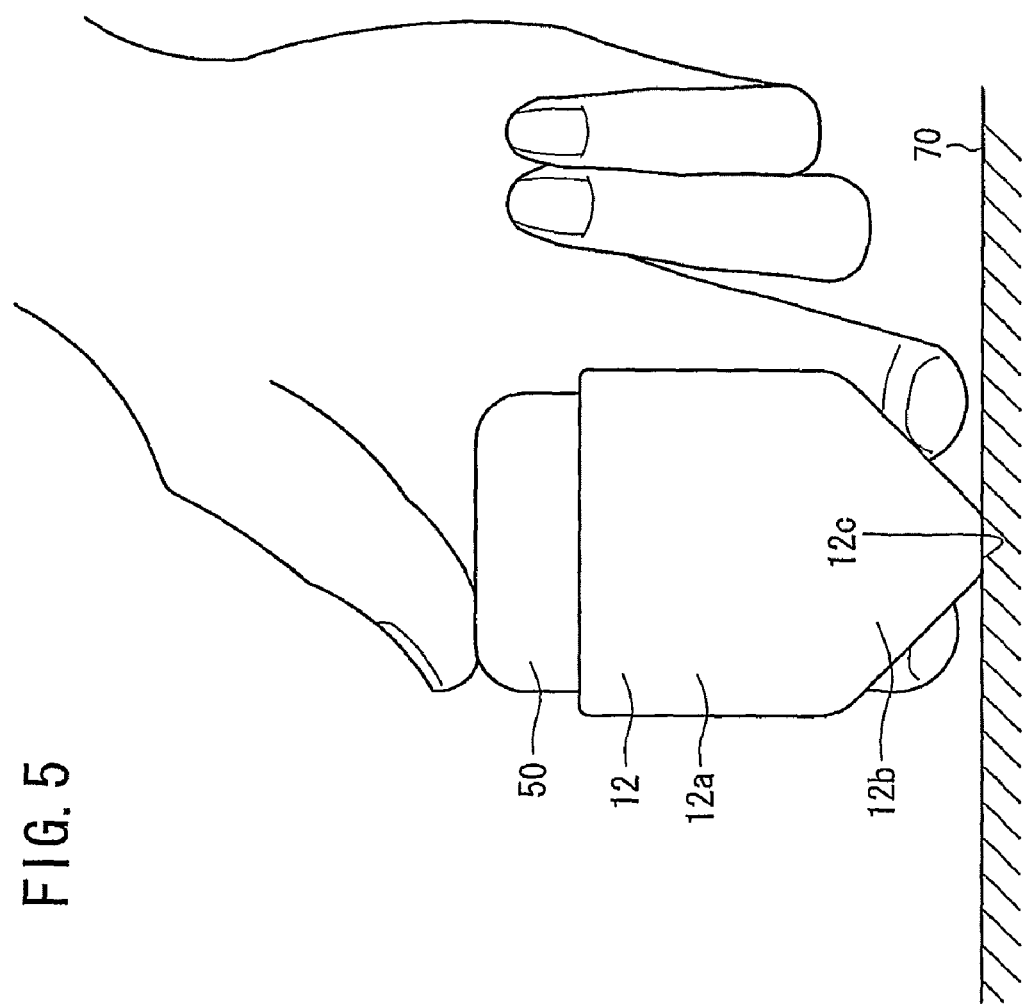
FIG. 5 is a schematic view showing the manner in which the puncture instrument is abutted on the skin.

Then, as shown in FIG. 5, the case 12 is held by hand to abut the distal end face 12c on the skin 70 of a patient, and the pusher button 50 is pushed into the inner cavity 22. At this time, the pusher button 50 may be pushed in by the thumb while the front portion 12b is being held between the index finger and the middle finger. The case 12 may have some projections as finger stops.

When the pusher button 50 is pushed in, the movable member 14 initially does not move because the protrusions 60 engage in the first recesses 26. When stronger force is applied to push the pusher button 50, the protrusions 60 are forced to move out of the first recesses 26. As the pusher button 50 is pushed under the stronger force and the walls 22a have nothing obstructive to the movement of the protrusions 60, the movable member 14 moves quickly forwardly. Accordingly, the movable member 14 ensures a certain puncture speed for the needle 40.

Figure 6:
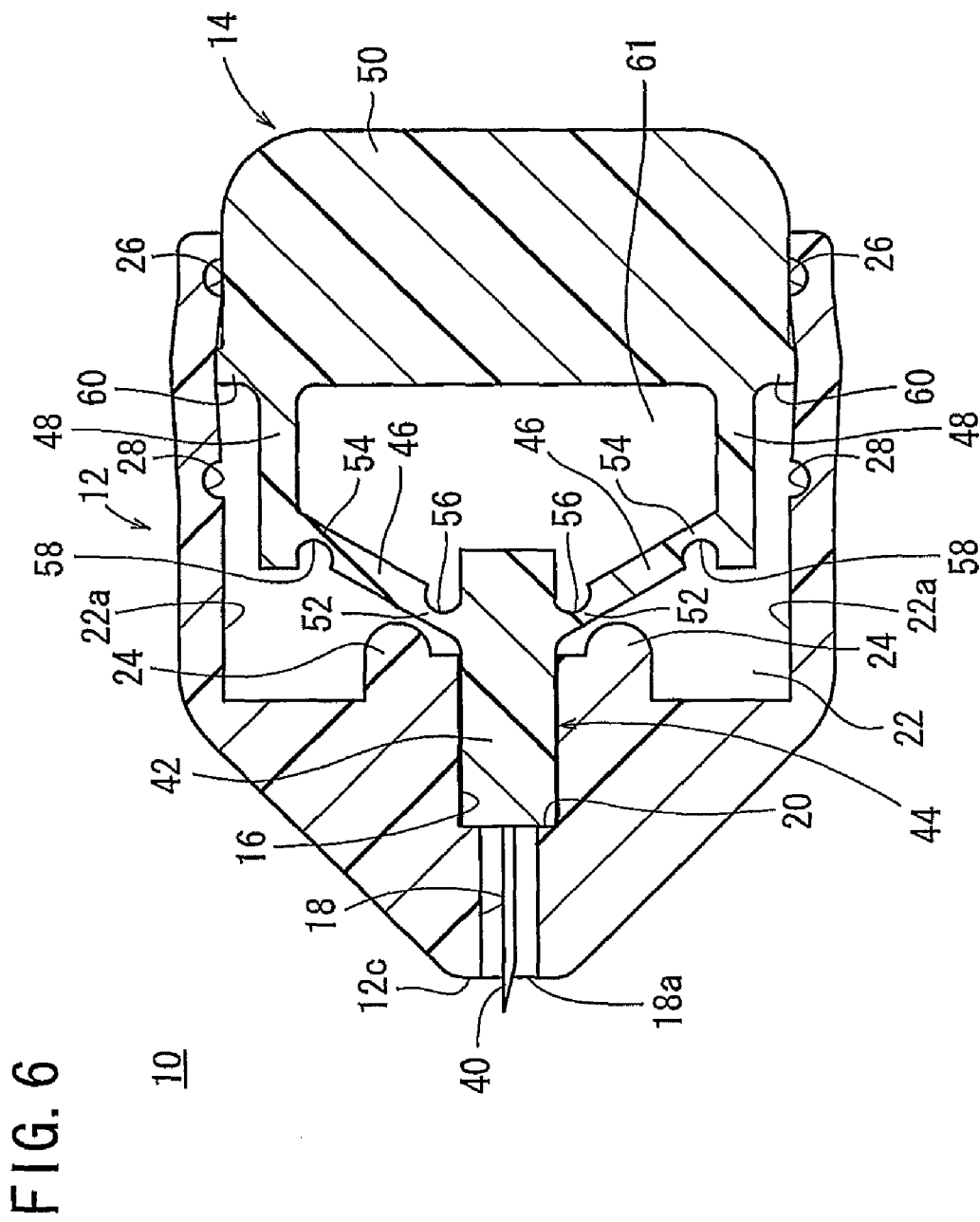
FIG. 6 is a cross-sectional view of the puncture instrument with a hub abutted against a step.

As shown in FIG. 6, when the movable member 14 moves forwardly, the tip end of the needle 40 projects from the distal end face 12c of the case 12 and punctures the skin. Specifically, the needle assembly 44 is not biased axially by an elastic body, but is pushed directly by the push rods 48 to cause the needle 40 to puncture the skin stably. The distance by which the needle 40 projects from the distal end face 12c is limited when the hub 42 engages the step 20 and is stopped thereby. Therefore, the needle 40 punctures the skin 70 to an appropriate depth.

Figure 7:
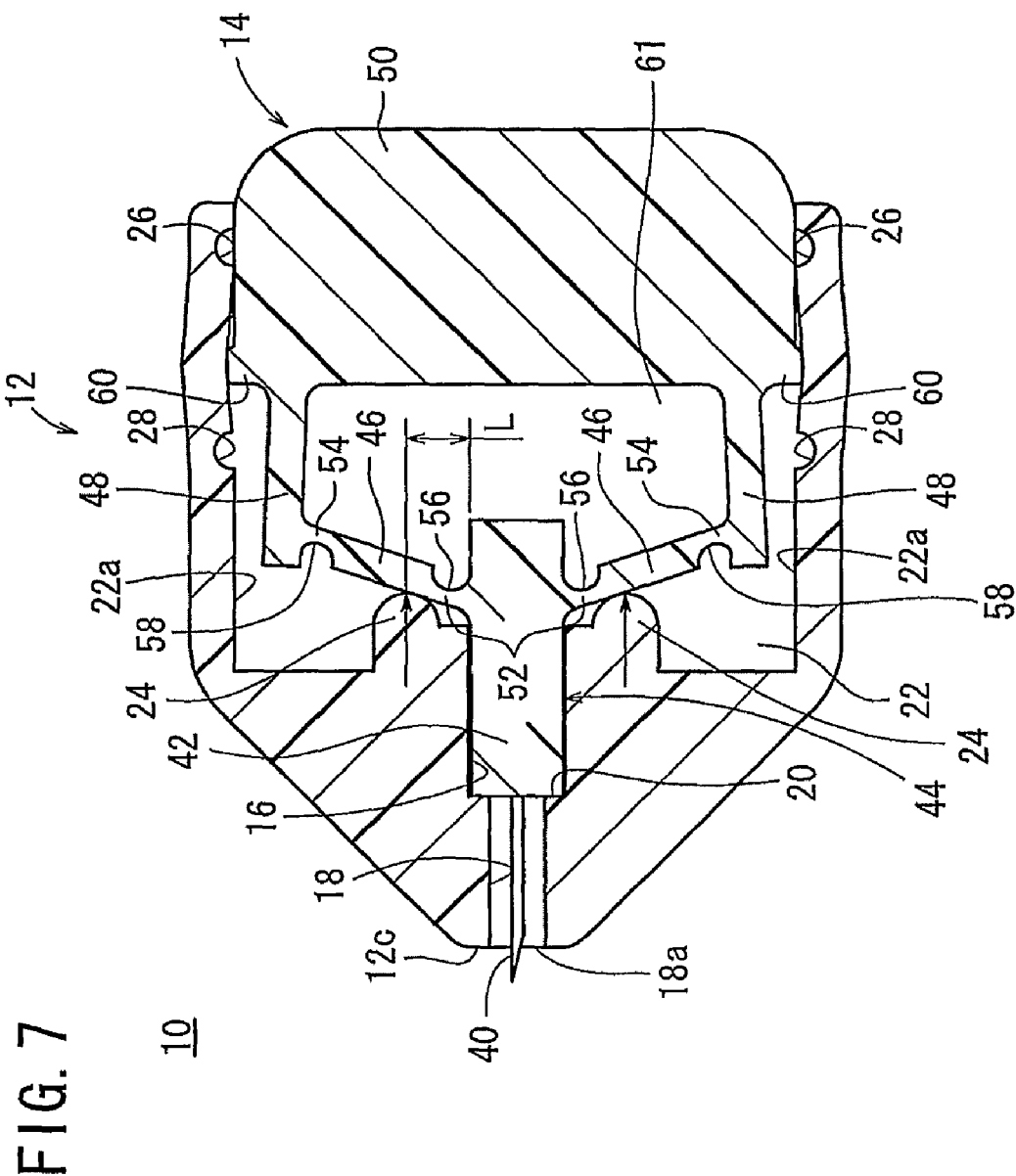
FIG. 7 is a cross-sectional view of the puncture instrument with arms abutted against fulcrum members.

As shown in FIG. 7, when the hub 42 engages the step 20, the needle assembly 44 stops moving forwardly among the movable member 14. Since the pusher button 50 is continuously pushed in, the arms 46 and the push rods 48 are further displaced forwardly, bringing front surfaces of the arms 46 into abutment with the fulcrum members 24. The fulcrum members 24 engage the front surfaces of the arms 46 near the first junctions 52 on the side opposite to the recesses 56.

Figure 8:
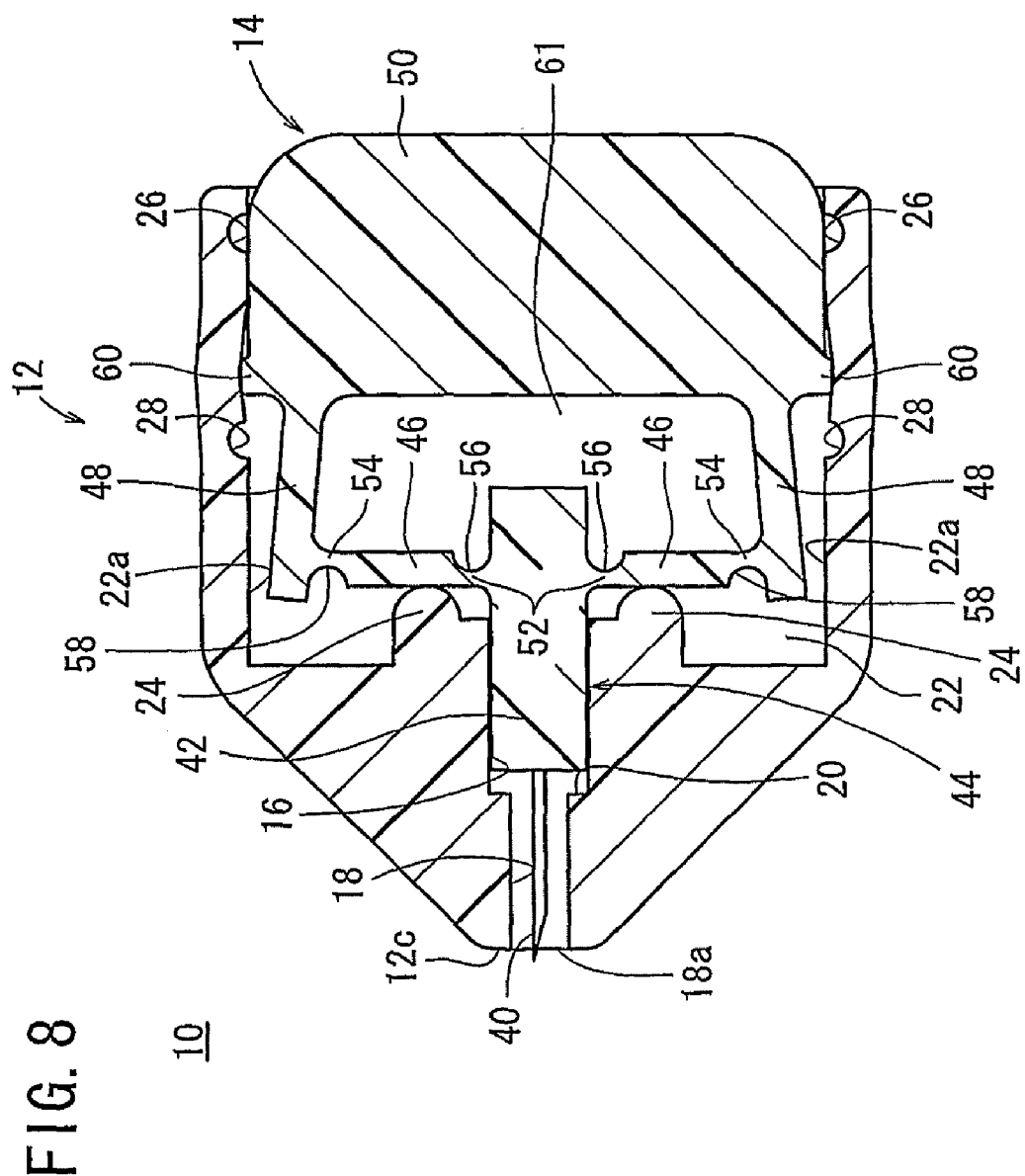
FIG. 8 is a cross-sectional view of the puncture instrument with the arms being turned about the fulcrum members.

As shown in FIG. 8, as the pusher button 50 is further pushed in, the push rods 48 and the pusher button 50 further move forwardly and then the arms 46 turn about the fulcrum members 24. At this time, the arms 46 smoothly turn about the fulcrum members 24 because the rear ends of the fulcrum members 24 are semicircular in cross-sectional shape.

Inasmuch as the fulcrum members 24 engage the arms 46 near the hub 42, the arms 46 are generally turned about the first junctions 52, causing arc motion of the second junctions 54 about the first junctions 52. The distal end of the push rods 48 are pushed outwardly. At this time, the push rods 48 act as leaf springs and are resiliently bent outwardly about the rear ends of the push rods 48. Since the push rods 48 act as leaf springs, they do not obstruct the turning movement of the arms 46, but allow the arms 46 to move stably.

When the arms 46 turn, stresses concentrate on the first junctions 52 and the second junctions 54 which are narrow so that the first junctions 52 and the second junctions 54 are plastically deformed beyond the elastic range.

The fulcrum members 24 which are positioned closely to the hub 42 are spaced from the hub 42 by certain distances L, respectively (see FIG. 7). As the second junctions 54 move forwardly, the first junctions 52 move rearward because the arms 46 are pivoted about the fulcrum members 24. The needle assembly 44 now starts moving rearward.

Figure 9:
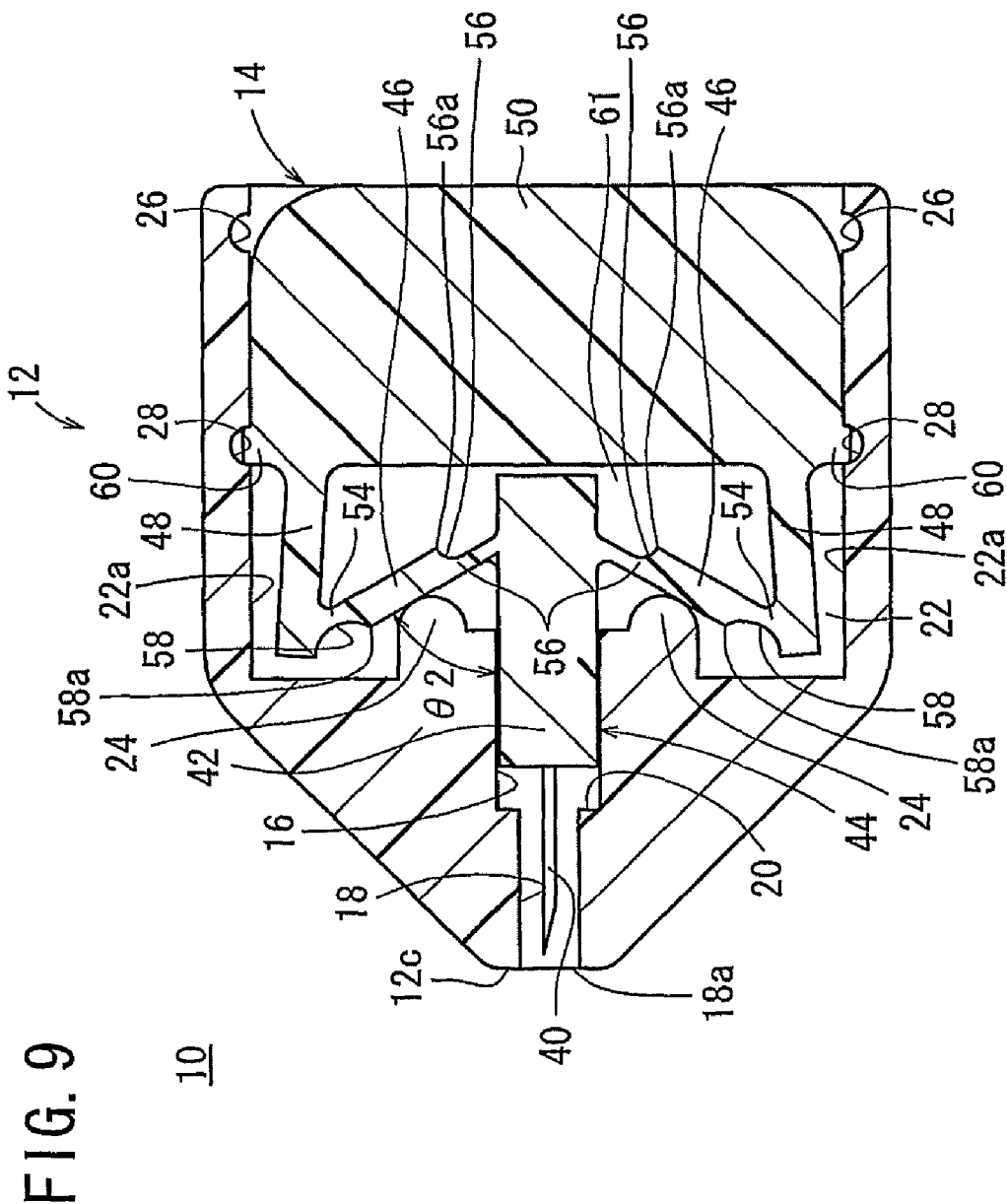
FIG. 9 is a cross-sectional view of the puncture instrument at the time the movable member has reached the end of its stroke.

As shown in FIG. 9, upon further forward movement of the push rods 48 and the pusher button 50 among the movable member 14, the arms 46 are further pivoted about the fulcrum members 24. The pusher button 50 reaches the end of its stroke and stops moving when the protrusions 60 engage in the second recesses 28.

At this time, the arms 46 are inclined forwardly in respective directions away from the longitudinal axis C of the hub 42. The needle assembly 44 is sufficiently retracted to pull the needle 40 out of the skin 70 into the needle passage 18. Since the arms 46 are turned about the fulcrum members 24 to pull back the needle assembly 44 rearward, the needle 40 is reliably pulled out of the skin 70. The arms 46 are inclined to the longitudinal axis C of the hub 42 at an angle θ2 of about 60°, for example. When the needle assembly 44 is fully retracted, the hub 42 enters the space 61 sufficient to both the hub 42 and the pusher button 50. Therefore, the needle assembly 44 does not interfere with the pusher button 50.

As the arms 46 are turned about the fulcrum members 24, the second junctions 54 are slightly displaced toward the longitudinal axis C of the hub 42, and the push rods 48 are also slightly displaced back toward the longitudinal axis C of the hub 42. Though the resilient force applied from the push rods 48 to the arms 46 is reduced, the force is strong enough to keep the needle assembly 44 pushed rearward.

At this time, the first junctions 52 and the second junctions 54 have been plastically deformed and may even have developed some cracking. Therefore, their resilient force has considerably been reduced to the point where the arms 46 can no longer restore their original attitude, i.e., the needle assembly 44 can no longer be pushed back forwardly, so that the arms 46 and the needle assembly 44 remain stably retracted. Since the first junctions 52 and the second junctions 54 are not fully broken, they keep holding the needle assembly 44 within the case 12. The pusher button 50 is prevented from being pulled out to use the puncture instrument 10 again.

The pusher button 50 is almost entirely or fully inserted in the inner cavity 22 and hence will not subsequently be operated carelessly. When the pusher button 50 has reached the end of its stroke, it is fully inserted in the inner cavity 22 or its rear end projects out of the inner cavity 22 by a distance of less than 5 mm, so that the pusher button 50 cannot be pulled back out of the inner cavity 22. The user can easily recognize whether the puncture instrument 10 is in a state before use or after use, simply by looking at how much the pusher button 50 projects out of the case 12.

Since the recesses 56 are formed in the rear surfaces of the arms 46 at the first junctions 52, when the arms 46 are turned about the fulcrum members 24, ends 56a of the recesses 56 move away from the hub 42 and are kept out of interference with the hub 42. Since the recesses 58 are formed in the front surfaces of the arms 46 at the second junctions 54, when the arms 46 are turned about the fulcrum members 24, ends 58a of the recesses 58 move away from the push rods 48 and are kept out of interference with the push rods 48.

The puncturing action illustrated in FIGS. 2, 6, 7, 8, and 9 is performed in a very short period of time, so that the tip end of the needle 40 projects instantaneously from the distal end opening 18a of the needle passage 18.

When the skin 70 is punctured by the needle 40, a small amount of blood flows out of the skin 70 and is sampled. The sampled blood is analyzed by a blood glucose meter or the like, not shown, to measure blood components. The puncture instrument 10 is thrown away after use. Since the needle 40 is fully retracted in the needle passage 18, it is free of the danger of being touched by anyone when the puncture instrument 10 is thrown away.

The puncture instrument 10 according to the first embodiment offers the following advantages. The puncture instrument 10 does not incorporate an elastic body for biasing the needle assembly 44 to move axially. Instead, the needle assembly 44 is pushed outwardly directly by the push rods 48 and the arms 46, causing the needle 40 to puncture the skin 70 stably. As the needle assembly 44 is pushed outwardly directly by the push rods 48 and the arms 46, the puncture instrument 10 does not need a mechanism for compressing an elastic body axially therein and subsequently triggering the resilient member to release its energy to push the needle assembly 44. Therefore, the puncture instrument 10 is relatively simple in structure. After the needle 40 has punctured the skin 70, the arms 46 are turned about the fulcrum members 24 to pull back the needle assembly 44 for thereby reliably pulling the needle 40 from the skin 70.

Since the puncture instrument 10 of simple structure can be mass-produced, it is inexpensive and suitable for use as a disposable product. The puncture instrument 10 is basically made up of two components, i.e., a composite assembly of the movable member 14 and the protective cap 15, and the case 12. Therefore, puncture instrument 10 is made up of a small number of parts, is simple in structure, and can easily be assembled.

The pusher button 50 may have recesses instead of the protrusions 60, and the case 12 may have protrusions instead of the first and second recesses 26, 28. The case 12 may have an air vent hole for allowing the movable member 14 to move smoothly therein.

A puncture instrument 100 according to a second embodiment of the present invention will be described below with reference to FIGS. 10 to 12. Those parts of the puncture instrument 100 which are identical to those of the puncture instrument 10 according to the first embodiment are denoted by identical reference characters, and will not be described in detail below.

Figure 10:
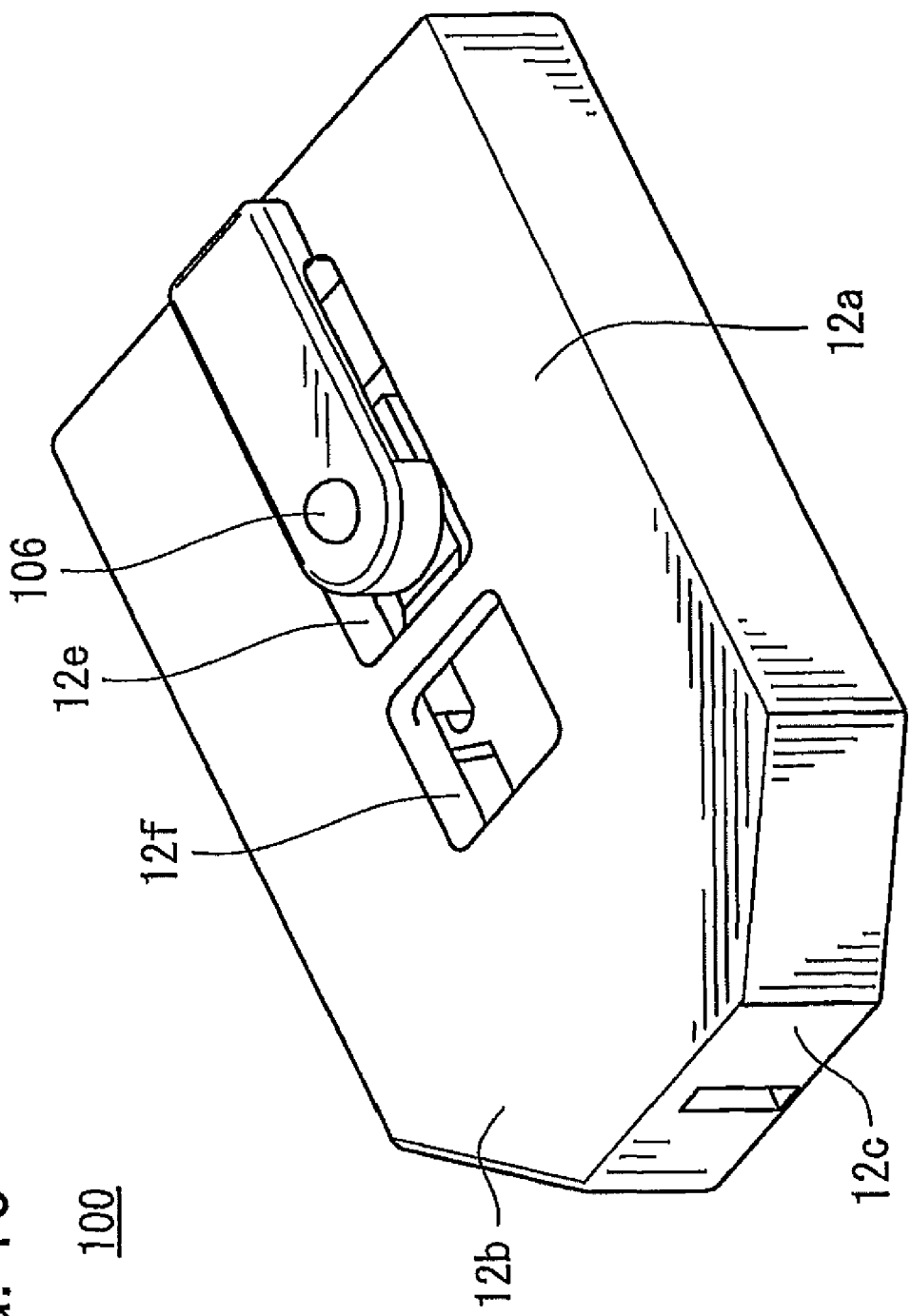
FIG. 10 is a perspective view of a puncture instrument according to a second embodiment of the present invention.
Figure 11:
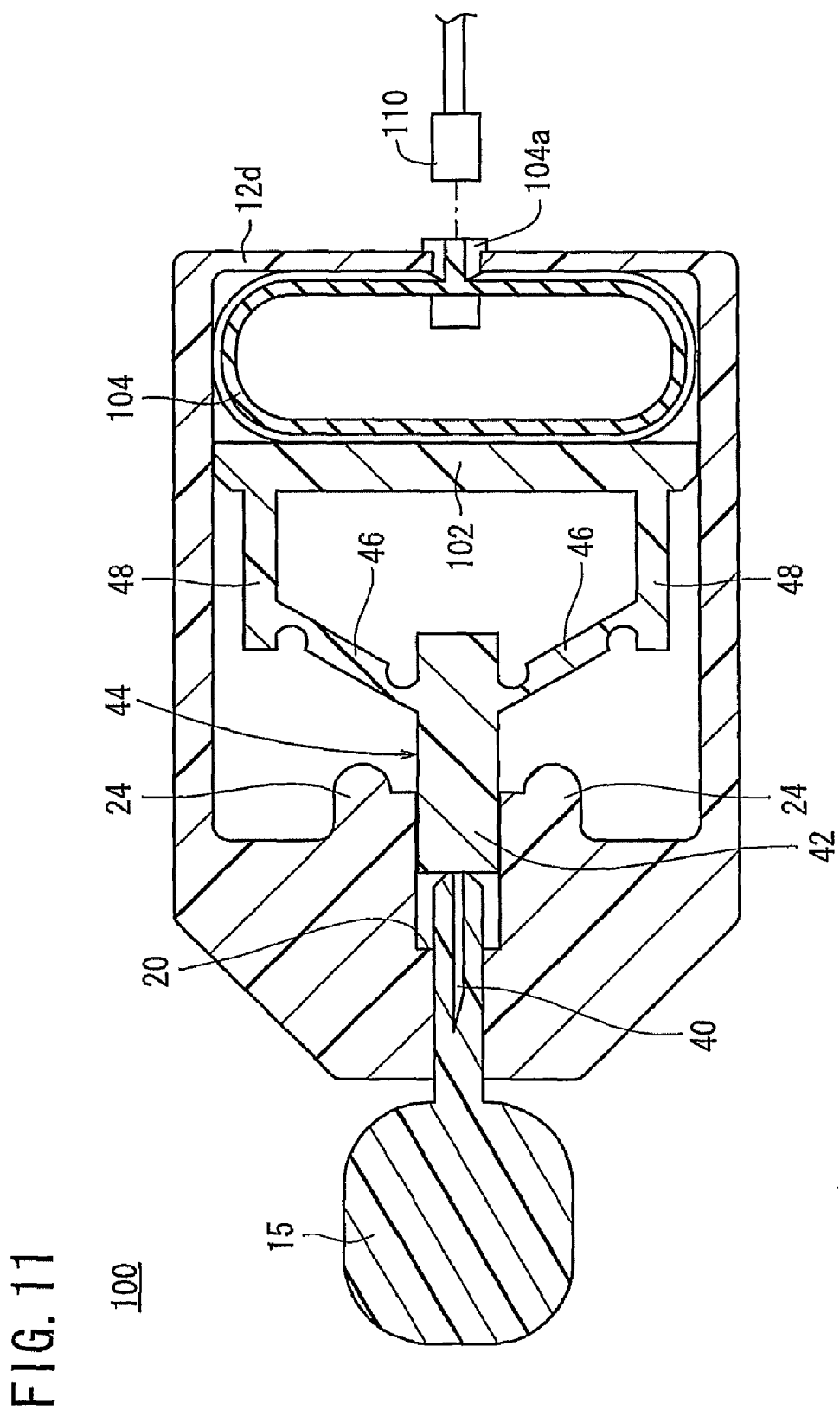
FIG. 11 is a cross-sectional view of the puncture instrument shown in FIG. 10, showing an initial state thereof.
Figure 12:
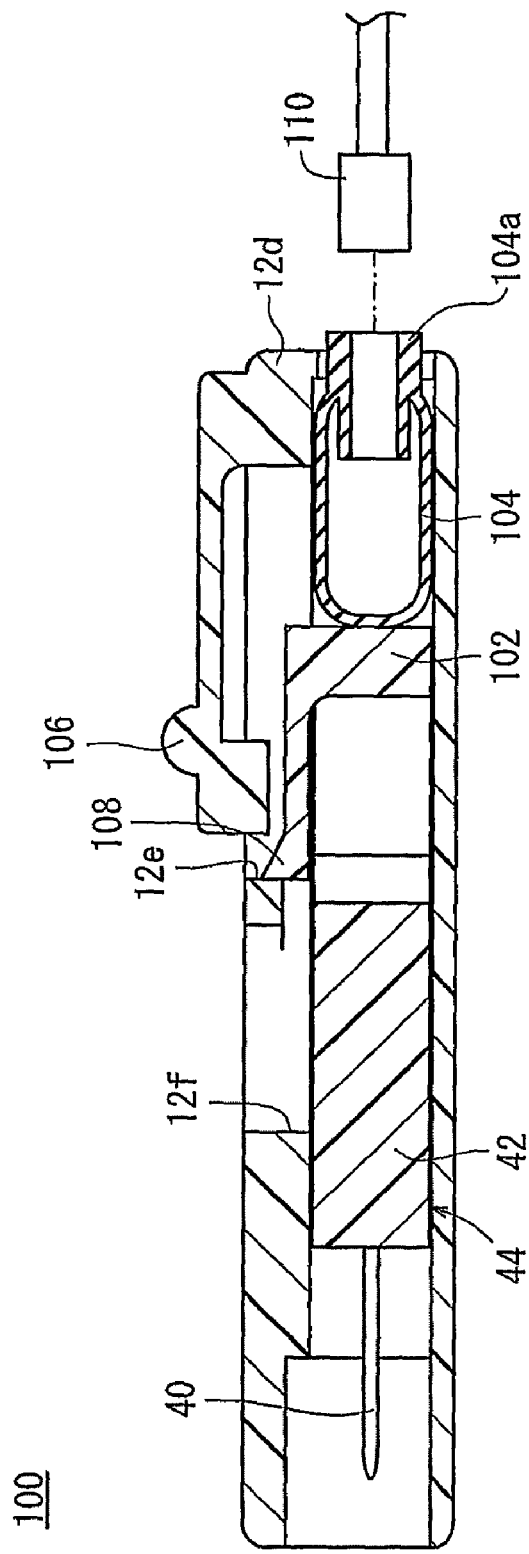
FIG. 12 is a sectional side view of the puncture instrument shown in FIG. 11.

As shown in FIGS. 10 to 12, the puncture instrument 100 according to the second embodiment comprises a pusher 102, a balloon (biasing means) 104 for biasing the pusher 102 to be pushed forwardly, a trigger switch (trigger) 106, and a stopper 108 for holding the pusher 102 against forward movement and releasing the pusher 102 to move forwardly when the trigger switch 106 is pressed. The pusher 102, the balloon 104, the trigger switch 106, and the stopper 108 are used to perform the function of the pusher button 50 of the puncture instrument 10 according to the first embodiment. Other details of the puncture instrument 100 according to the second embodiment are basically the same as those of the puncture instrument 10 according to the first embodiment.

The case 12 includes a rear end wall 12d covering the rear end of the inner cavity therein. The balloon 104 is disposed in a closed space between the pusher 102 and the rear end wall 12d. The pusher 102 is constitutively identical to the front end of the pusher button 50 of the puncture instrument 10 according to the first embodiment. The two push rods 48 are connected to the pusher 102. The rear end wall 12d has a central hole defined therein which holds therein an air supply port 104a of the balloon 104. A compressed air supply tube 110 in a hospital can be removably connected to the air supply port 104a.

The stopper 108 has a rear end connected to the pusher 102 and extends forwardly therefrom. The stopper 108 has a front end lightly engaging an end face of a first upper hole 12e formed in the upper wall of the case 12. The trigger switch 106 has a rear end connected to the rear end wall 12d of the case 12 and extends forwardly therefrom. The trigger switch 106 essentially covers the first upper hole 12e. The trigger switch 106 is disposed above and extends along the stopper 108.

The case 12 also has a second upper hole 12f formed in the upper wall thereof more closely to the distal end than the first upper hole 12e. The user of the puncture instrument 100 can confirm through the second upper hole 12f the position of the movable member 14 to see if the puncture instrument 100 is in a state before use or after use. The puncture instrument 100 is free of the protrusions 60, the first recesses 26, and the second recesses 28 of the puncture instrument 10 according to the first embodiment.

The puncture instrument 100 operates as follows: First, the protective cap 15 is removed, and the compressed air supply tube 110 is connected to the air supply port 104a to introduce compressed air into the balloon 104, thereby pressurizing the balloon 104. When the balloon 104 is pressurized, it biases the pusher 102 forwardly. However, the pusher 102 is held at rest because the stopper 108 engages the end face of the first upper hole 12e.

Then, the user holds the case 12, abuts the distal end face 12c on the skin 70, and then presses the trigger switch 106. The trigger switch 106 is resiliently depressed to bring the stopper 108 out of engagement with the end face of the first upper hole 12e. The movable member 14 is released and pushed quickly forwardly by the expanding balloon 104, causing the needle 40 to puncture the skin 70. Thereafter, the arms 46 are turned about the fulcrum members 24 to pull back the needle 40 from the skin 70 into the needle passage 18.

The puncture instrument 100 offers the same advantages as those of the puncture instrument 10 according to the first embodiment. Furthermore, the pusher 102 is pushed by the balloon 104, and the trigger switch 106 can be operated with light force.

Insofar as the air pressure is used to push the pusher 102, the balloon 104 may be replaced with a diaphragm or a bellophragm. A packing may be fitted around the pusher 102 and slidably held in contact with the inner wall surface of the case 12, so that the pusher 102 and the case 12 jointly operate as a piston-cylinder mechanism.

A puncture instrument 200 according to a third embodiment of the present invention will be described below with reference to FIG. 13. Those parts of the puncture instrument 200 which are identical to those of the puncture instruments 10, 100 according to the first and second embodiments are denoted by identical reference characters, and will not be described in detail below.

Figure 13:
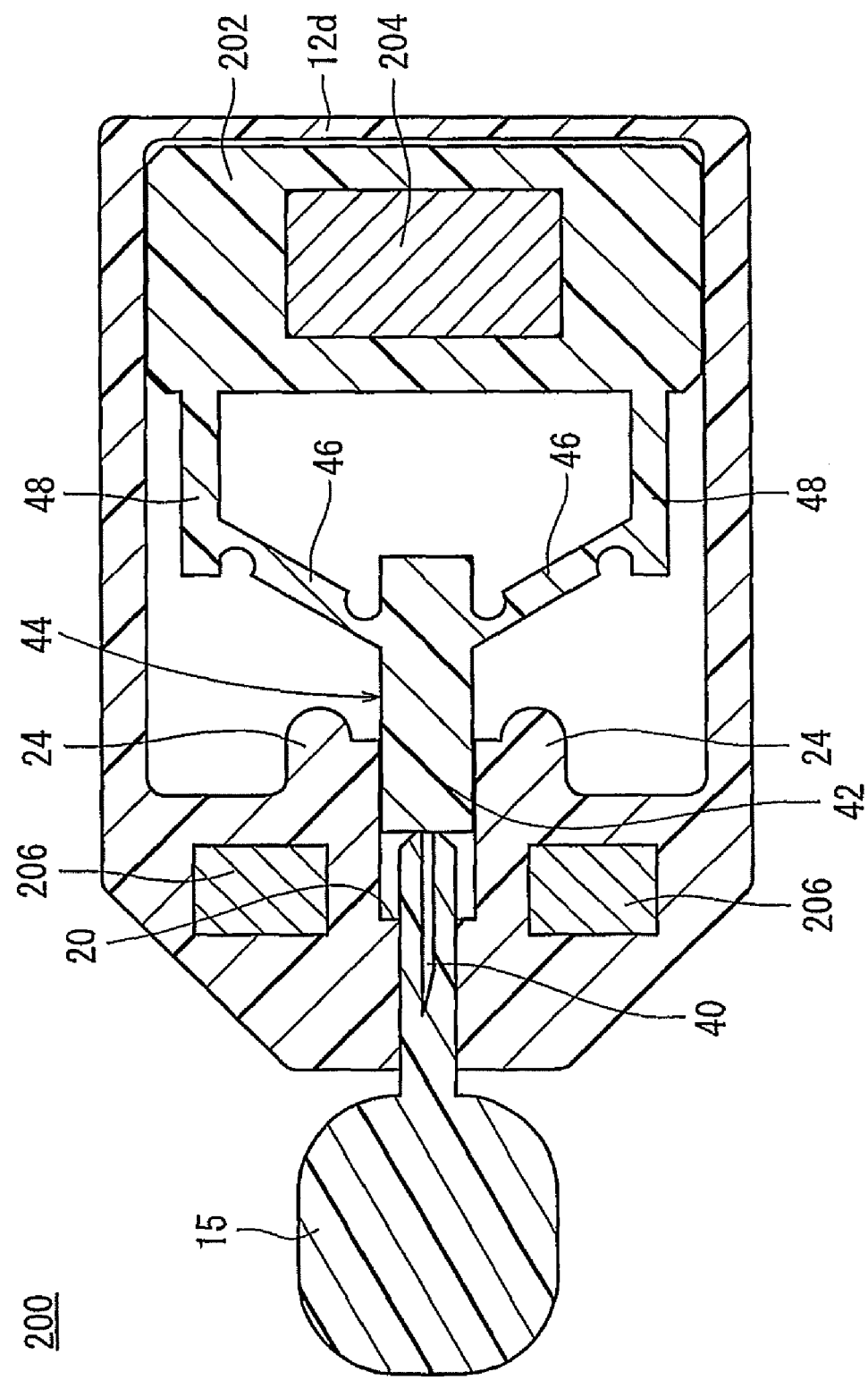
FIG. 13 is a perspective view of a puncture instrument according to a third embodiment of the present invention, showing an initial state thereof.

As shown in FIG. 13, the puncture instrument 200 comprises a pusher 202, a main magnet (biasing means) 204 disposed in the pusher 202, and a pair of auxiliary magnets (biasing means) 206 disposed symmetrically in the front portion 12b of the case 12. The two push rods 48 are connected to the pusher 202 as with the pusher button 50 of the puncture instrument 10. The puncture instrument 200 includes the trigger switch 106, the stopper 108, the rear end wall 12d, the first upper hole 12e, and the second upper hole 12f as with the puncture instrument 100.

The main magnet 204 and the auxiliary magnets 206 are oriented such that their N and S poles face each other to magnetically attract each other for thereby biasing the pusher 202 to be pushed forwardly.

The puncture instrument 200 operates as follows: The pusher 202 is normally biased to move forwardly under magnetic forces from the main magnet 204 and the auxiliary magnets 206. However, the pusher 202 is held at rest because the stopper 108 engages the end face of the first upper hole 12e. When the user holds the case 12, abuts the distal end face 12c on the skin 70, and then presses the trigger switch 106, the stopper 108 is released out of engagement with the end face of the first upper hole 12e, and the movable member 14 is released and pushed forwardly, causing the needle 40 to puncture the skin 70. Thereafter, the arms 46 are turned about the fulcrum members 24 to pull back the needle 40 from the skin 70 into the needle passage 18.

The puncture instrument 200 offers the same advantages as those of the puncture instrument 100 according to the second embodiment. Furthermore, the puncture instrument 200 does not require an external power source such as a compressed air source because the pusher 202 is normally biased forwardly under magnetic force from the main magnet 204 and the auxiliary magnets 206.

The case 12 of the puncture instrument 200 may have holes for removing therethrough the auxiliary magnets 206 and the main magnet 204 after it has reached the end of its stroke.

Modifications of the puncture instruments 10, 100, 200 will be described below.

Figure 14A:
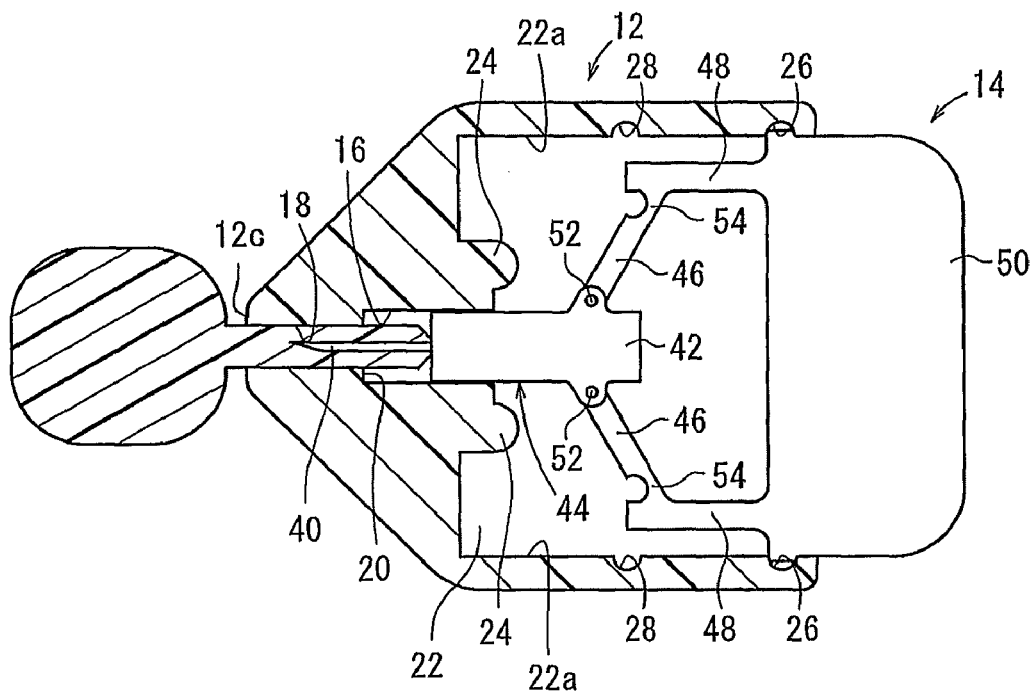
FIG. 14A is a cross-sectional view showing arms according to a first modification in an initial state thereof.
Figure 14B:
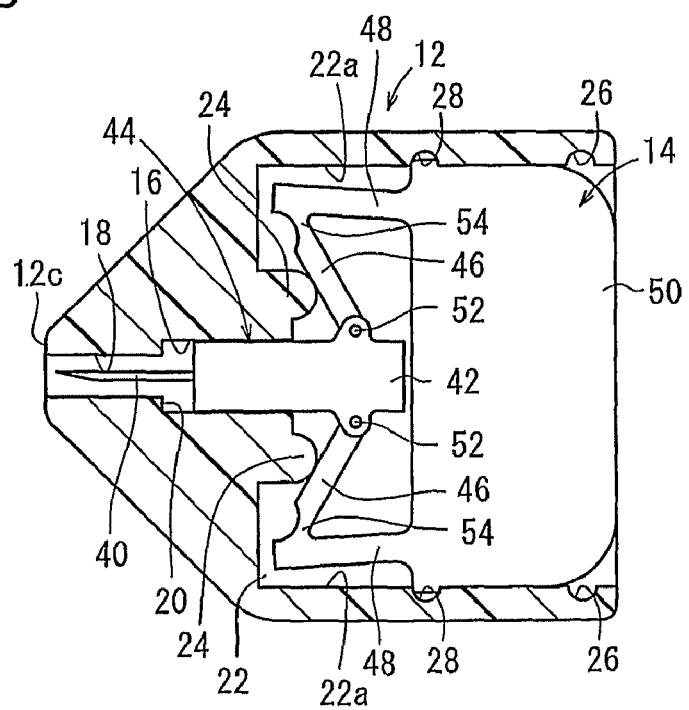
FIG. 14B is a cross-sectional view showing the arms according to the first modification at the time the movable member has reached the end of its stroke.

According to a first modification, as shown in FIG. 14A, the first junctions 52 of the arms 46 are rotatably supported on the hub 42. When the arms 46 are rotated about the first junctions 52, the second junctions 54 are plastically deformed as shown in FIG. 14B.

Alternatively, the second junctions 54 may be rotatably supported on the push rods 48, and the first junctions 52 may be plastically deformed. In other words, as long as at least the first junctions 52 or the second junctions 54 are plastically deformable, the movable member 14 is stably held at the end of its stroke.

Figure 15:
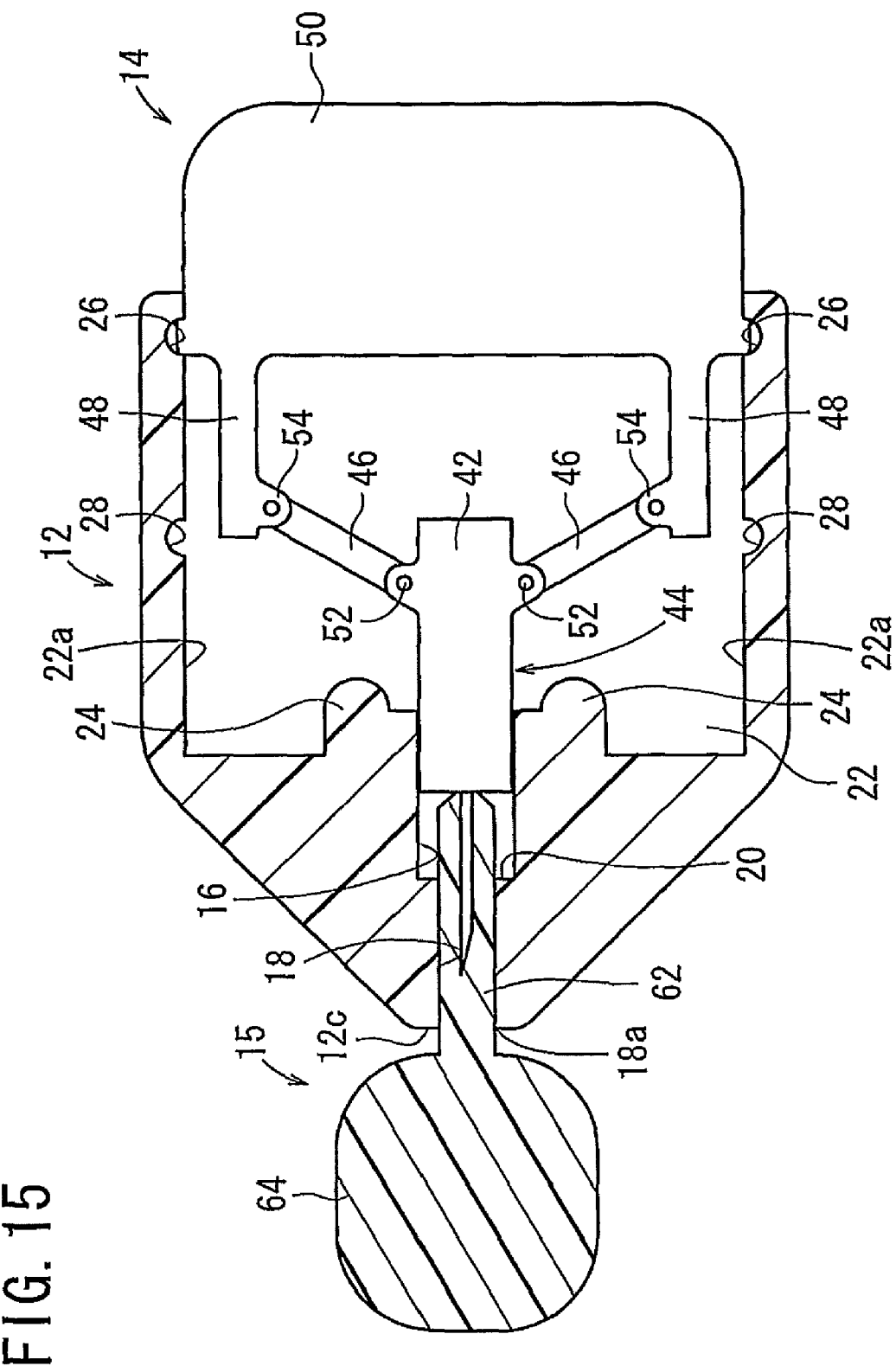
FIG. 15 is a cross-sectional view showing arms according to a second modification.

According to a second modification, as shown in FIG. 15, the first junctions 52 of the arms 46 are rotatably supported on the hub 42, and the second junctions 54 are rotatably supported on the push rods 48.

Figure 16:
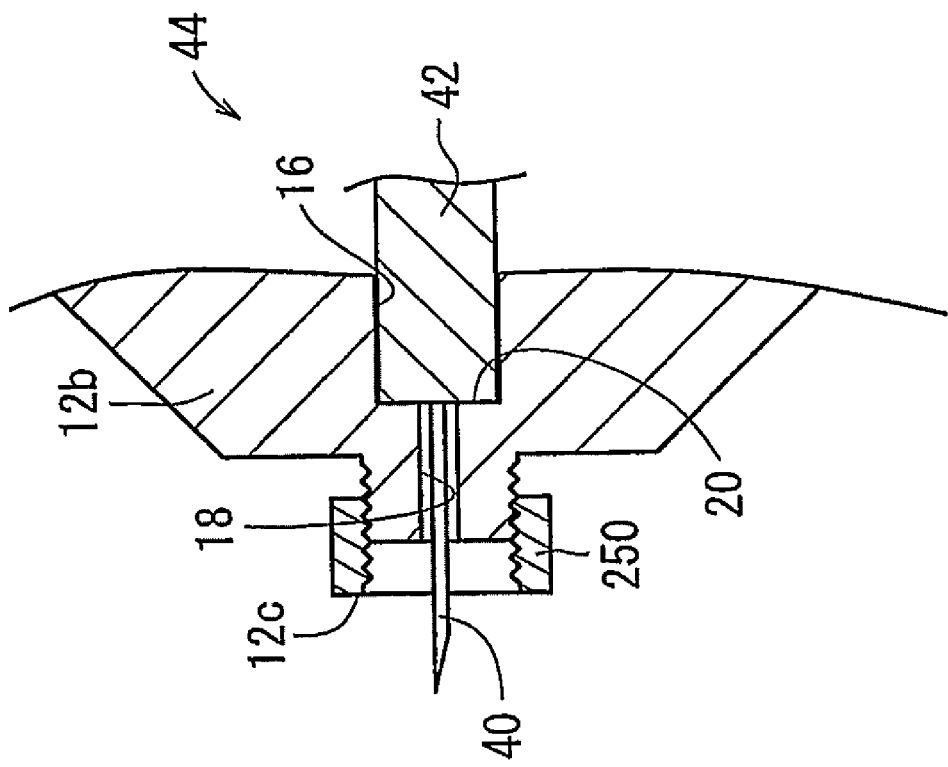
FIG. 16 is an enlarged cross-sectional view of a distal end portion of a modified puncture instrument which is combined with a nut for adjusting the projection of a needle.
Figure 17:
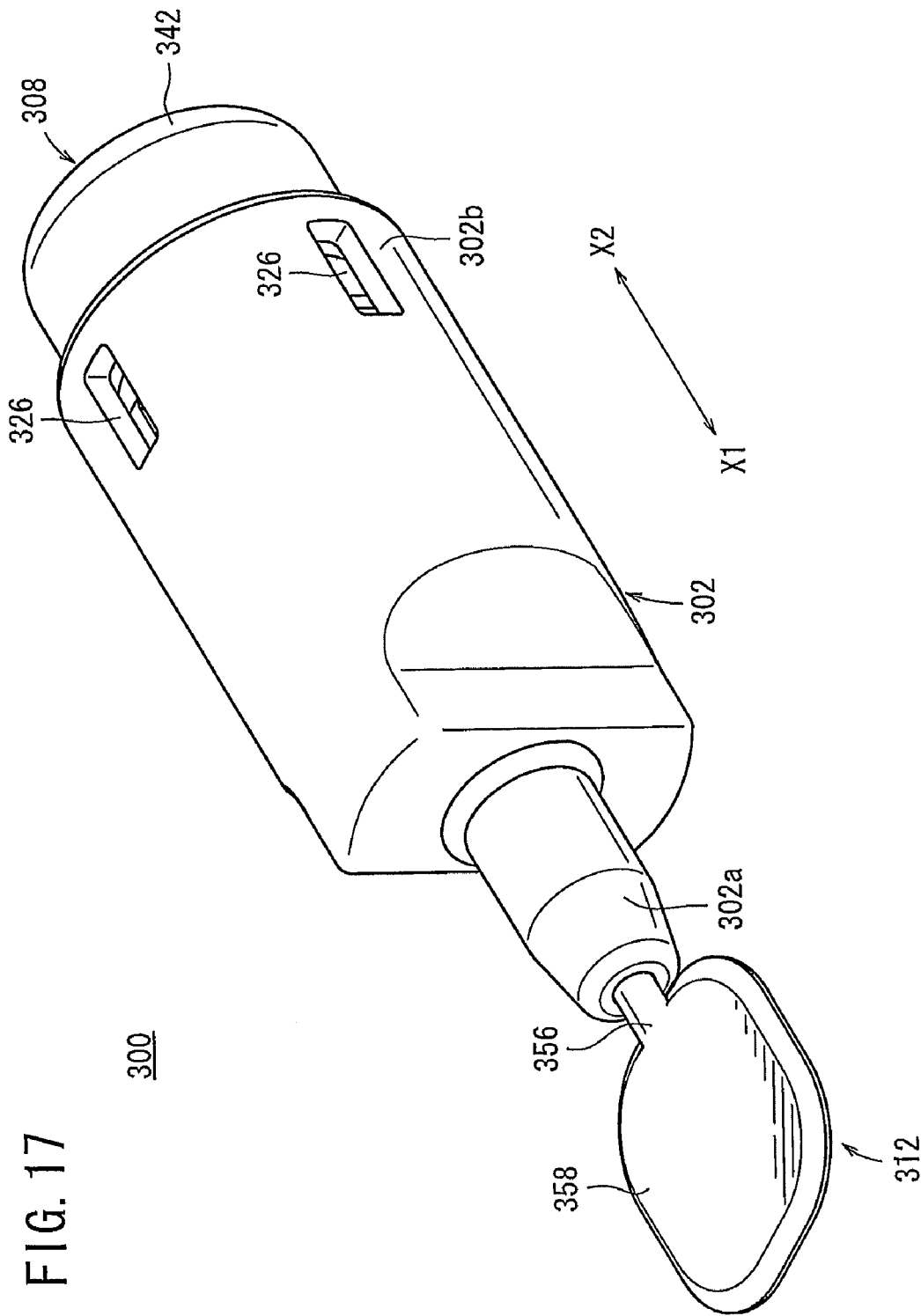
FIG. 17 is a perspective view of a puncture instrument according to a fourth embodiment of the present invention.

FIG. 16 shows another modified puncture instrument in which the distal end face 12c is provided by a nut 250 threaded over the distal end of the front portion 12b. When the nut 250 is turned about its own axis, the distance between the distal end face 12c and the step 20 is changed to adjust the distance by which the needle 40 projects from the distal end face 12c. The nut 250 may have an indexing mechanism for setting itself to several angular positions about its own axis. Any of various other mechanisms may be employed to adjust the distance by which the needle 40 projects from the distal end face 12c.

A puncture instrument 300 according to a fourth embodiment of the present invention will be described below with reference to FIGS. 17 to 22. Those parts of the puncture instrument 300 which are identical to those of the puncture instruments 10, 100, 200 according to the first, second, and third embodiments are denoted by identical reference characters, and will not be described in detail below.

As shown in FIGS. 17 to 22, the puncture instrument 300 comprises a body 302, a hub holder 304 displaceably disposed in the body 302, a hub 306 held on an end of the hub holder 304 and supporting a needle 40, a pusher 308 for pushing the hub holder 304 forwardly, a link mechanism 310 for transferring pressing force applied to the pusher 308 to the hub holder 304, and a protective cap 312 mounted on the body 302.

The body 302 is of a hollow, substantially cylindrical structure and has a tapered front end portion 302a in which the needle 40 is inserted and a rear end portion 302b that is greater in diameter than the front end portion 302a. The pusher 308 is partly exposed from the rear end portion 302b.

The body 302 has a hub passage 314 and a needle passage 316 formed in the front end portion 302a and extending axially therethrough. The needle passage 316 has an end that is open at the front end portion 302a of the body 302 and an opposite end communicating with the hub passage 314. The needle passage 316 is smaller in diameter than the hub passage 314, with a first step 318 being disposed between the needle passage 316 and the hub passage 314.

The rear end portion 302b of the body 302 has an inner cavity 320 formed therein, and the pusher 308 is inserted in the inner cavity 320. The inner cavity 320 communicates with the hub passage 314 through a holder hole 322 that is formed centrally in the body 302. The inner cavity 320 is of a circular cross-sectional shape and is open at the rear end portion 302b. The holder hole 322 is of a substantially rectangular cross-sectional shape, and the hub holder 304 is displaceably disposed in the holder hole 322. A second step 324 is provided between the holder hole 322 and the hub passage 314.

The rear end portion 302b of the body 302 has a plurality of guide grooves 326 formed therein at circumferentially equally spaced angular intervals. The pusher 308 has a plurality of protrusions 328, to be described later, inserted respectively in the guide grooves 326. The guide grooves 326 have a predetermined length in the axial directions, indicated by the arrows X1, X2, of the body 302. The inner cavity 320 of the body 302 communicates with the exterior of the body 302 through the guide grooves 326.

A pair of fulcrum members 330a, 330b is disposed on the inner wall surface of the holder hole 322 in alignment with the axis of the body 302. The fulcrum members 330a, 330b extend a predetermined distance rearward from the inner wall on the hub passage 314 side and have ends of a semicircular cross-sectional shape. The fulcrum members 330a, 330b are disposed in confronting relation to each other across the hub holder 304 that is disposed in the holder hole 322.

A pair of guide slots 332 is formed in another inner wall surface of holder hole 322 at respective positions that are angularly spaced from the fulcrum members 330a, 330b by 90°. The guide slots 332 extend axially of the body 302.

The hub holder 304 comprises a base 334 having a substantially rectangular shape and a hollow cylindrical hub support 336 projecting axially forwardly from the base 334. The base 334 has guide rails 338 disposed on respective opposite side surfaces thereof and projecting transversely therefrom. The guide rails 338 slidably engage respectively in the guide slots 332 for guiding the hub holder 304 axially in the directions indicated by arrows X1, X2 without allowing the hub holder 304 to rotate about its own axis in the body 302.

The base 334 has a pair of arm holes 340 formed therethrough at respective positions that are transversely spaced a predetermined distance from each other across the axis of the base 334. The link mechanism 310 includes two arms 350a, 350b disposed respectively on upper and lower surfaces of the base 334 and having respectively ends pivotally supported in the arm holes 340, as described later.

The hub support 336 projects from the front end of the base 334. The hub 306 has a rear end fitted in the front end of the hub support 336, and hence is supported by the hub support 336.

The pusher 308 comprises a cylindrical button 342 and a pair of push rods 344a, 344b projecting from the front end of the button 342. The button 342 is partly housed in the inner cavity 320 of the body 302. A plurality of protrusions 328 are disposed on an outer circumferential surface of the button 342 and inserted respectively in the guide grooves 326 of the body 302. Since the guide grooves 326 extend in the axial direction of the body 302, the pusher 308 is guided displaceably in the axial directions indicated by the arrows X1, X2.

Figure 18:
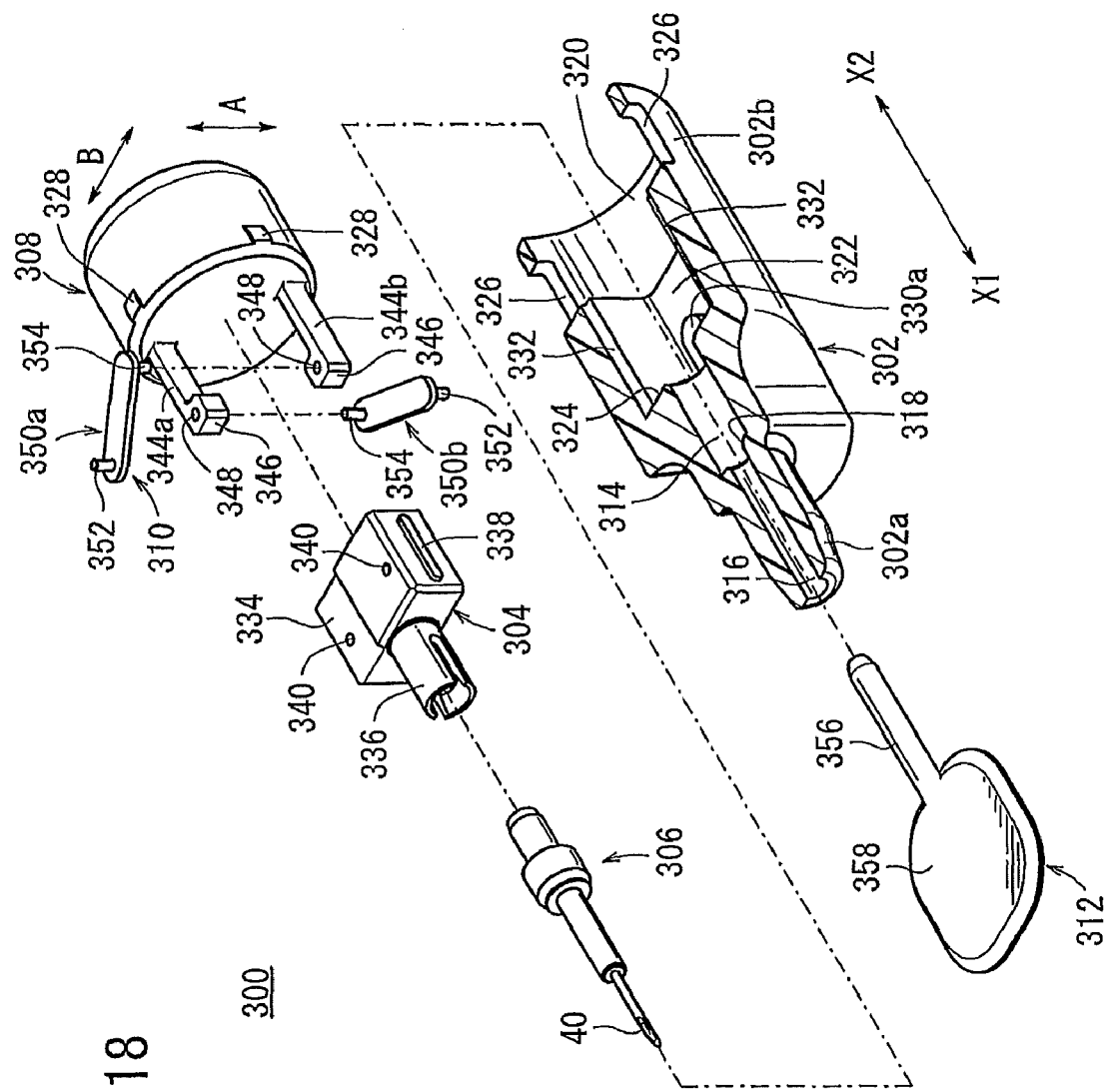
FIG. 18 is an exploded perspective view, partly shown in cross section, of the puncture instrument shown in FIG. 17.

The push rods 344a, 344b are offset with respect to the center of the button 342 and project axially linearly a predetermined distance from the button 342. Specifically, as shown in FIG. 18, the push rods 344a, 344b are vertically spaced from each other across the center of the button 342 by a predetermined distance in the directions indicated by the arrow A and are also horizontally spaced from each other across the center of the button 342 by a predetermined distance in the directions indicated by the arrow B.

The push rods 344a, 344b have respective wider supports 346 on their distal ends. The other ends of the arms 350a, 350b are pivotally supported on the respective supports 346. The supports 346 have respective link holes 348 formed therein perpendicularly to the push rods 344a, 344b and extending vertically through the supports 346 parallel to each other, as shown in FIG. 18.

The arms 350a, 350b of the link mechanism 310 have respective first pins 352 on ends thereof and respective second pins 354 on the other ends thereof.

The first and second pins 352, 354 project perpendicularly to the axes of the arms 350a, 350b. The first pins 352 project in one direction, and the second pins 354 project in the opposite direction. The first pins 352 are inserted respectively in the arm holes 340 of the hub holder 304, and the second pins 354 are inserted respectively in the link holes 348 of the push rods 344a, 344b. The first pins 352 function as a first junction connected to the hub holder 304, and the second pins 354 as a second junction connected to the push rods 344a, 344b.

Figure 19:
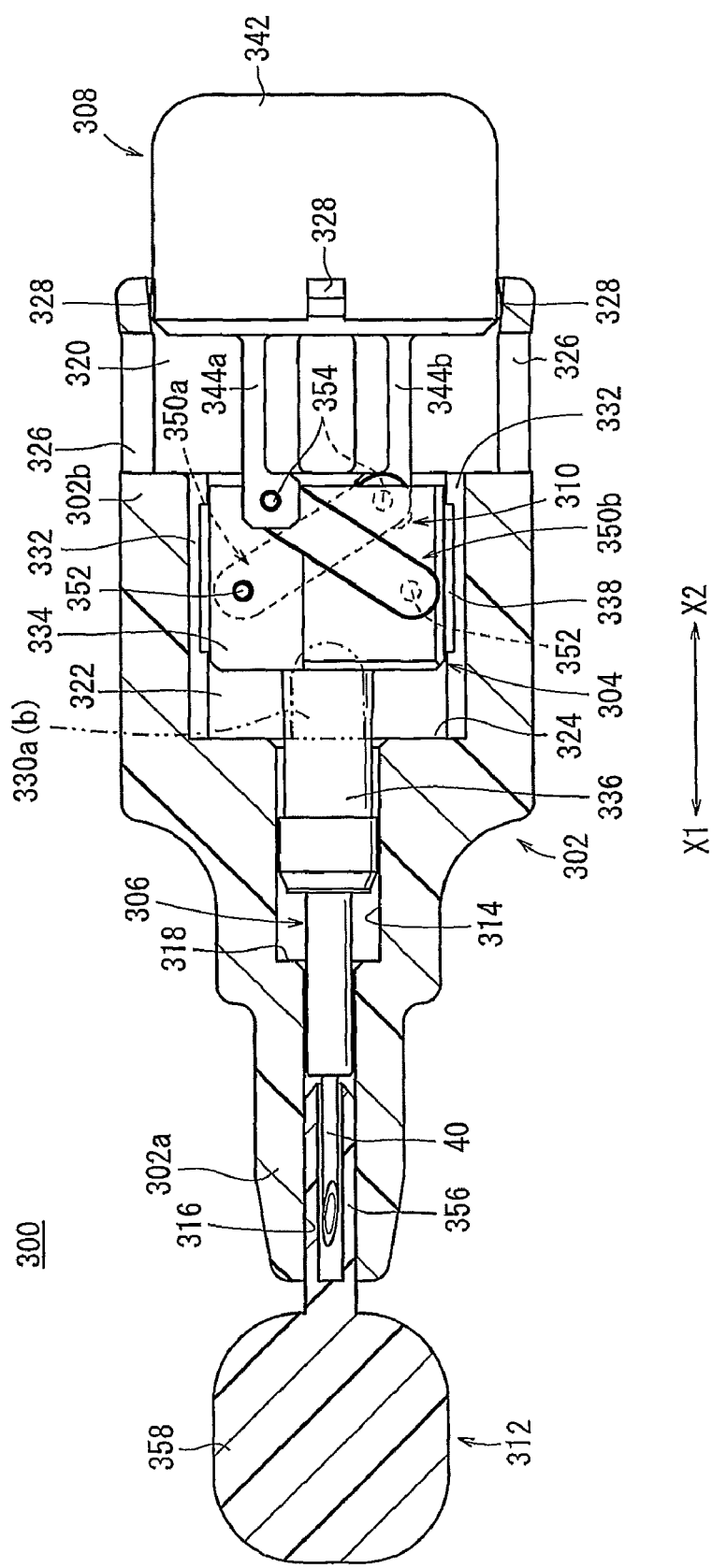
FIG. 19 is a cross-sectional view of the puncture instrument shown in FIG. 17, showing the puncture instrument in a state ready for puncture.

When the puncture instrument 300 is in a state ready for puncture, i.e., before the puncture instrument 300 is used to puncture the skin 70, the arms 350a, 350b are disposed one on each side of the hub holder 304 in mutually crossing relation to each other as shown in FIG. 19.

The protective cap 312 comprises a tubular member 356 inserted in the needle passage 316 and covering the needle 40, and a tab 358 connected to the front end of the tubular member 356. The tubular member 356 is inserted and fitted in the needle passage 316. The tubular member 356 may be fixed to the needle passage 316 by fusion, adhesive bonding, or the like. The protective cap 312 is irradiated with γ-rays, electron beams, or the like to sterilize the needle 40 in the tubular member 356.

The puncture instrument 300 operates as follows: In the state ready for puncture as shown in FIG. 19, the tab 358 of the protective cap 312 is twisted to release the tubular member 356 out of fitting engagement with the body 302, thereby removing the protective cap 312.

Then, the body 302 is held by hand to abut the front end portion 302a on the skin (not shown), and the button 342 of the pusher 308 is pushed toward the body 302 in the direction indicated by the arrow X1. At this time, the button 342 may be pushed in by the thumb while the region of the body 302 near the front end portion 302a is being held between the index finger and the middle finger.

When the pusher 308 is pushed, since the protrusions 328 engage the inner wall surface of the inner cavity 320, the pusher 308 is initially limited somewhat in its displacement. As the pushing forces applied to the pusher 308 are increased, the protrusions 328 are displaced out of engagement with the inner wall surface of the inner cavity 320 and inserted into the guide grooves 326 (see FIG. 20). The pusher 308 is now guided to move in the axial direction of the body 302 toward the front end portion 302a of the body 302 in the direction indicated by the arrow X1.

Figure 20:
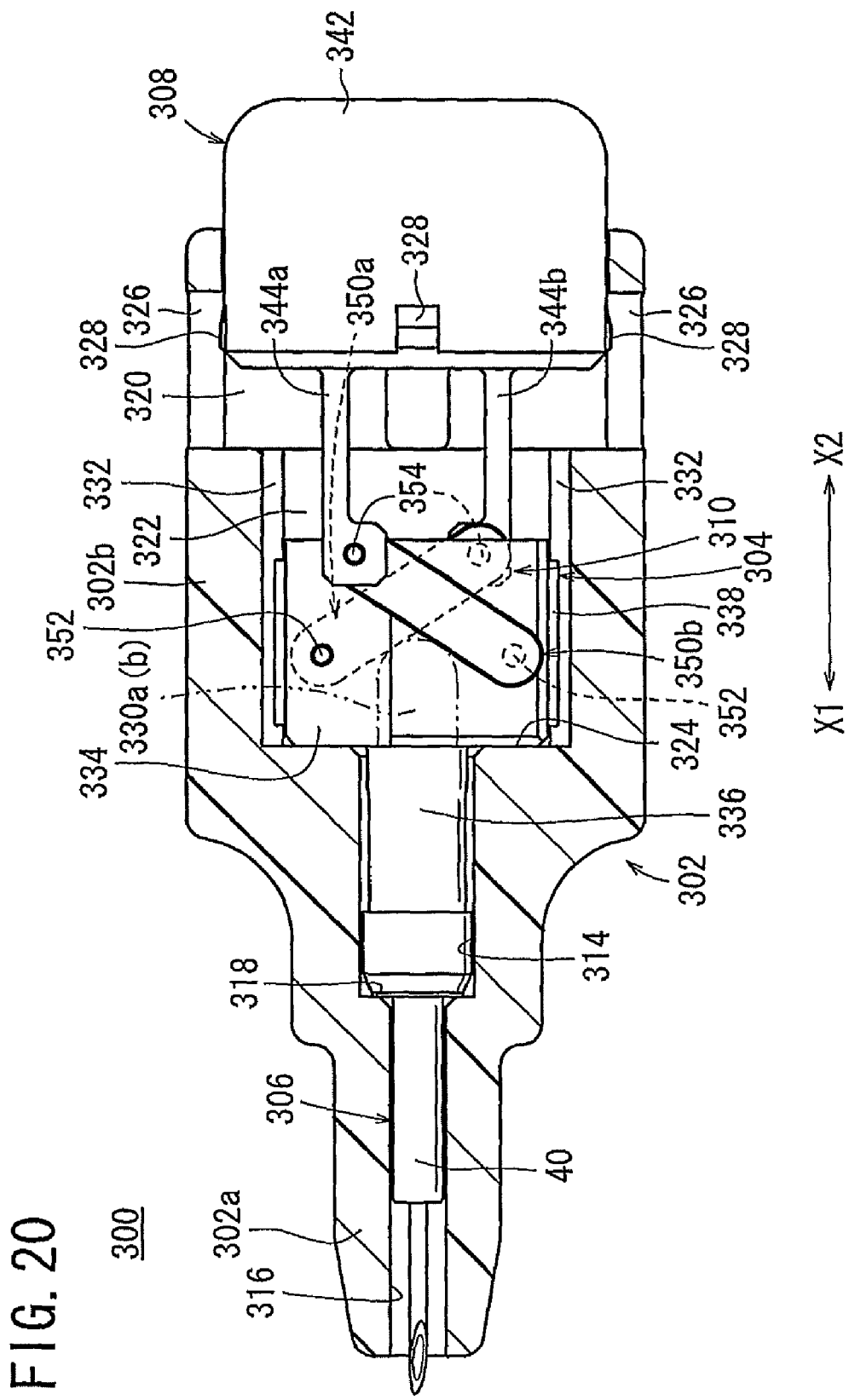
FIG. 20 is a cross-sectional view of the puncture instrument shown in FIG. 17, showing the manner in which after a protective cap is removed from the puncture instrument a needle punctures the skin of a patient.

When the pusher 308 is displaced toward the front end portion 302a as shown in FIG. 20, the arms 350a, 350b pivotally supported by the push rods 344a, 344b and the hub holder 304 are displaced toward the front end portion 302a, displacing the hub 306 held by the hub holder 304 along the hub passage 314 and the needle passage 316. At this time, the arms 350a, 350b do not turn, but are displaced in unison with the pusher 308 and the hub holder 304. Stated otherwise, the arms 350a, 350b are kept as struts between the hub holder 304 and the pusher 308.

The hub holder 304 is displaced only axially without being rotated about its own axis because it is guided by the guide rails 338 engaging in the respective guide slots 332.

The tip end of the needle 40 projects from the front end portion 302a of the body 302 and punctures the skin. Specifically, the needle 40 is not biased axially by an elastic body, but is pushed directly by the push rods 344a, 344b and the hub holder 304 as the pusher 308 is pushed. The axial displacement of the needle 40 is limited when the hub 306 engages the first step 318, so that the distance by which the needle 40 projects from the front end portion 302a of the body 302 is controlled. Therefore, the needle 40 punctures the skin to an appropriate depth.

Figure 21:
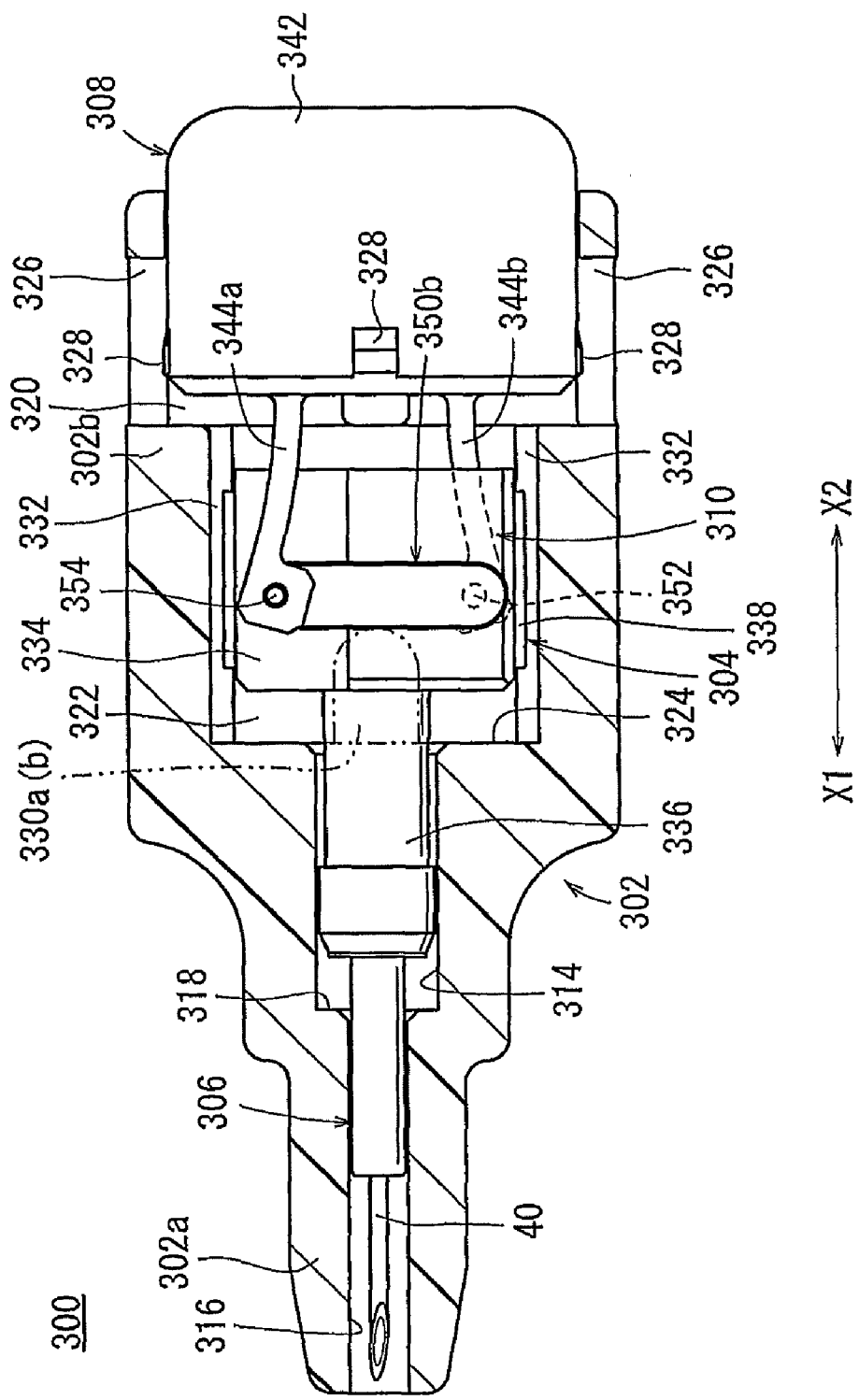
FIG. 21 is a cross-sectional view of the puncture instrument shown in FIG. 17 with arms abutted against fulcrum members and turning.

As shown in FIG. 21, when the pusher 308 is further pushed in, the arms 350a, 350b gradually turn about the second pins 354 by the push rods 344a, 344b. The turn of the arms 350a, 350b pulls the hub holder 304 toward the pusher 308 in the direction indicated by the arrow X2, because the arms 350a, 350b have their substantially central regions abutting against the ends of the fulcrum members 330a, 330b, and turn about the abutting regions from the initial angular position of the arms 350a, 350b with respect to the hub holder 304 and the pusher 308. The hub 306 held by the hub holder 304 is displaced in a direction into the body 302, retracting the needle 40 into the needle passage 316.

When the arms 350a, 350b turn, since the arms 350a, 350b are limited against displacement in the axial directions of the body 302 by the fulcrum members 330a, 330b, the push rods 344a, 344b which hold the ends of the arms 350a, 350b are elastically deformed such that their supports 346 move toward the opposite side wall surfaces of the holder hole 322.

Figure 22:
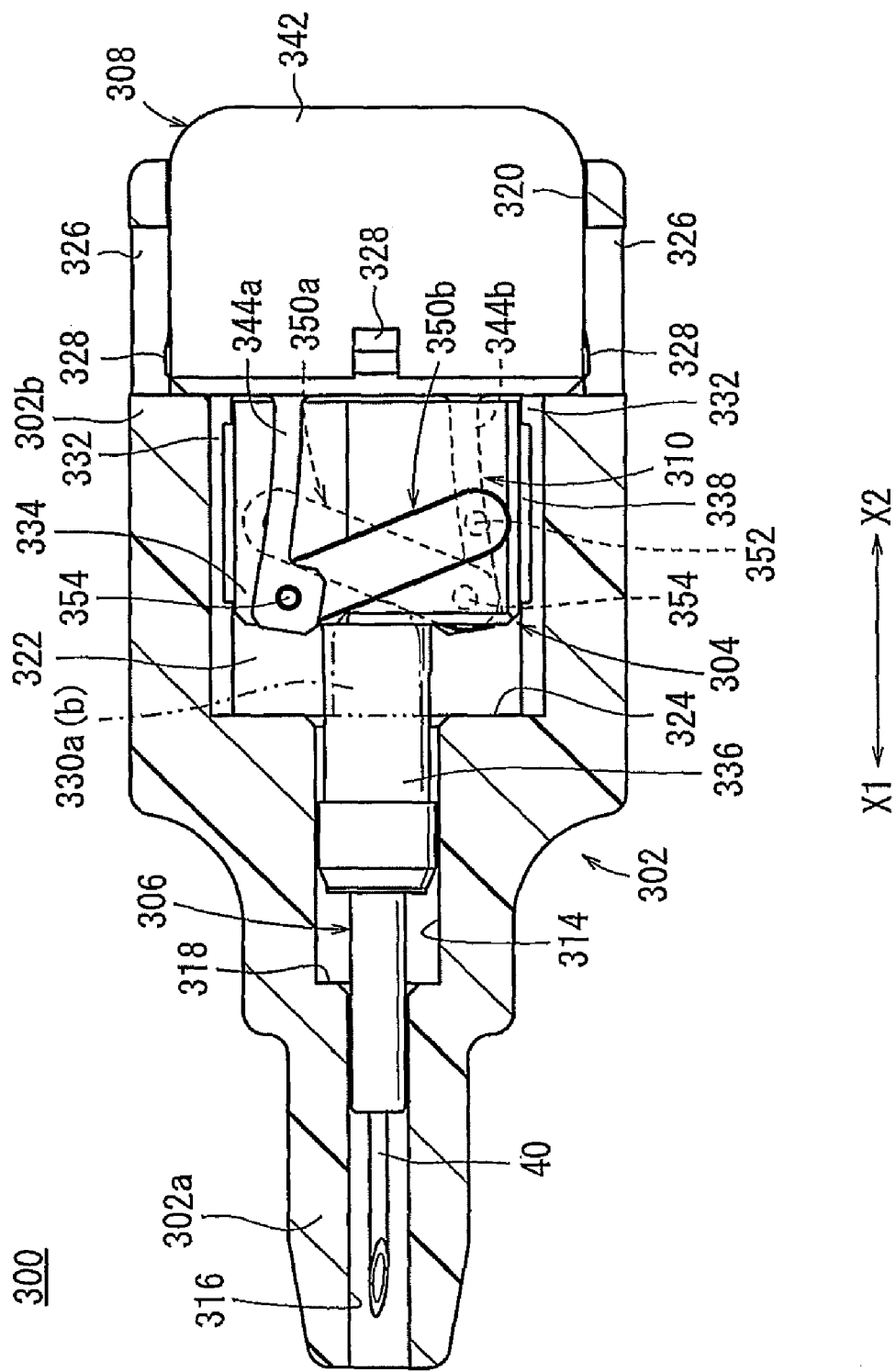
FIG. 22 is a cross-sectional view of the puncture instrument shown in FIG. 17 at the time a pusher has reached the end of its stroke.
Figure 23:
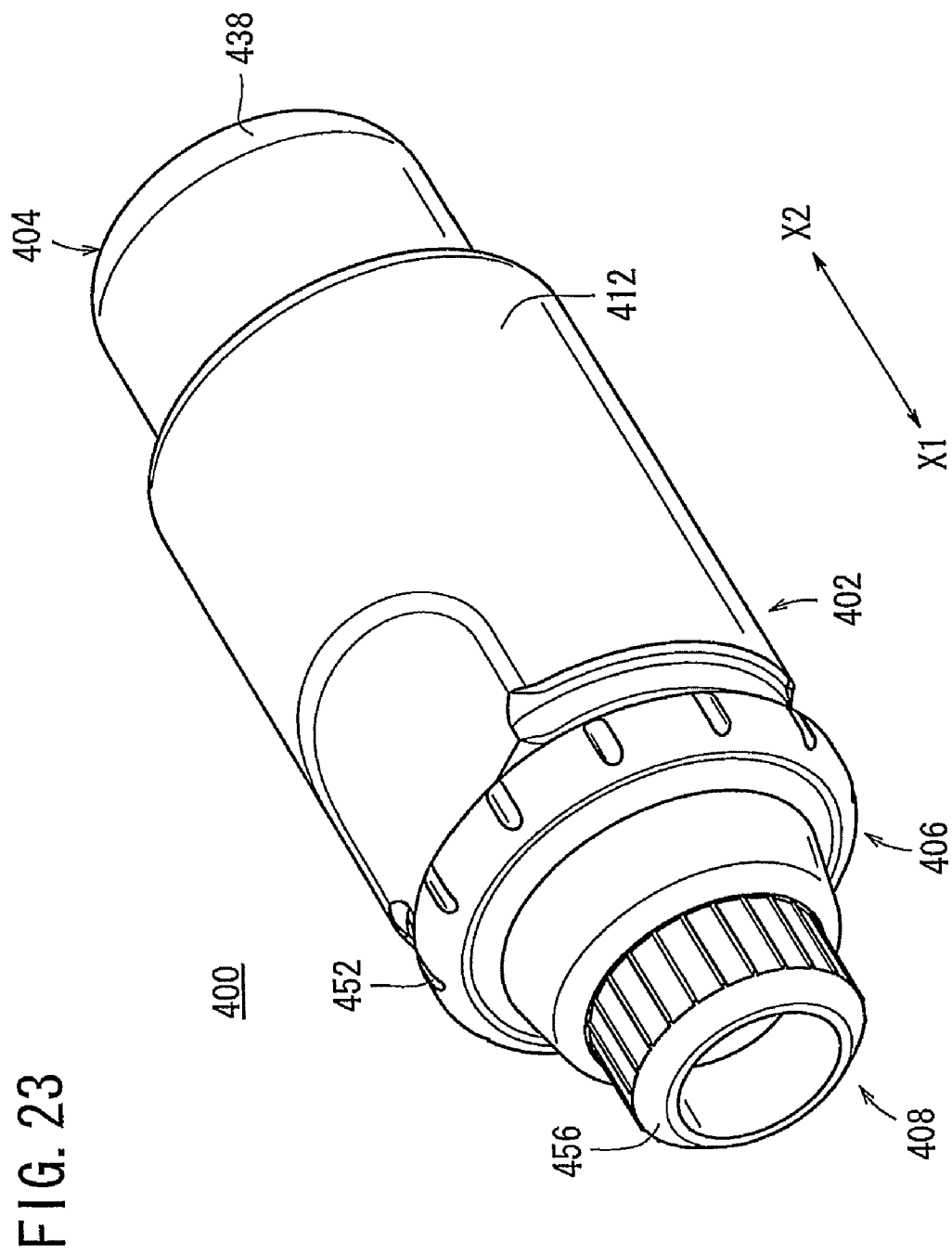
FIG. 23 is a perspective view of a puncture instrument according to a fifth embodiment of the present invention.
Figure 24:
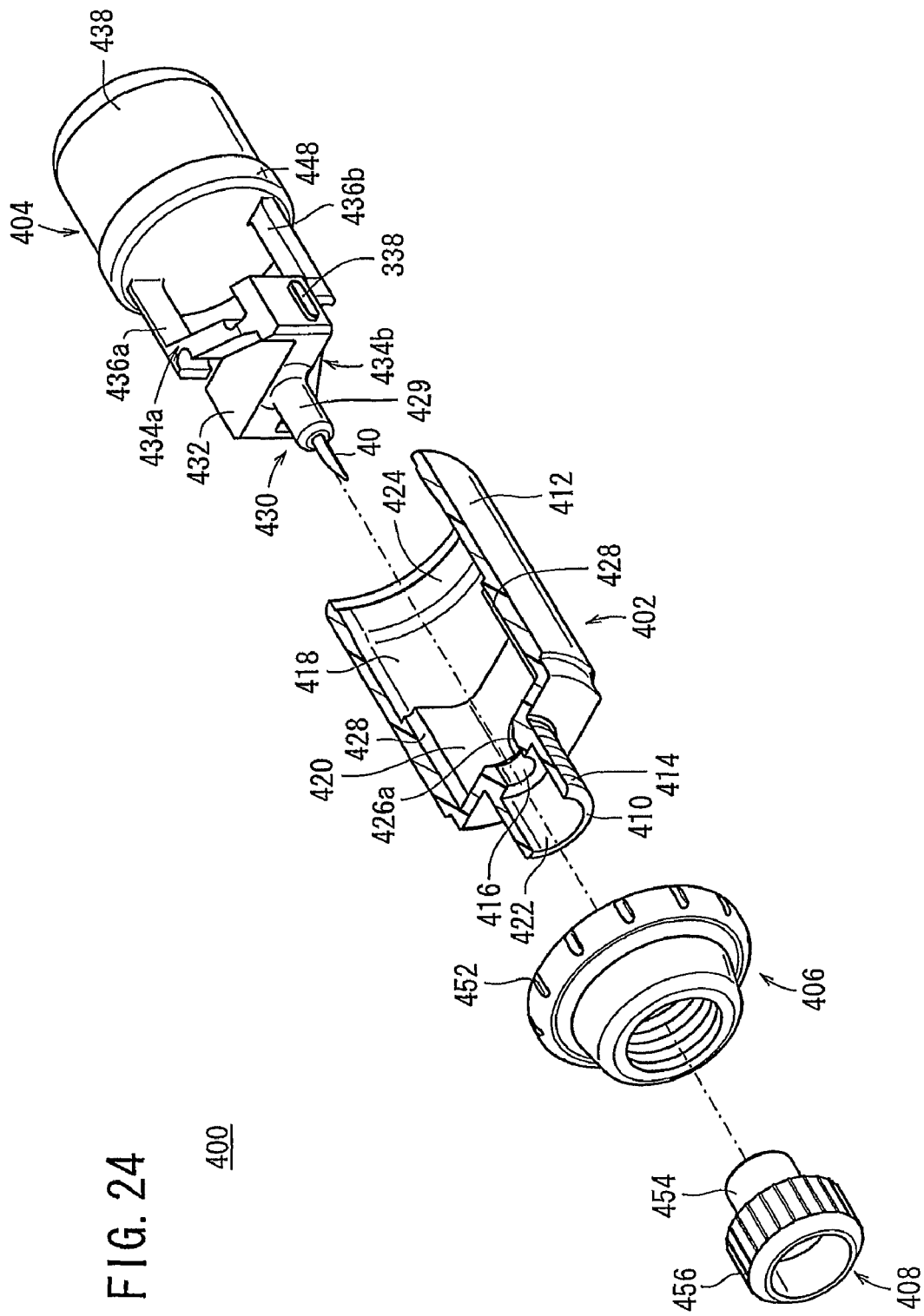
FIG. 24 is an exploded perspective view, partly shown in cross section, of the puncture instrument shown in FIG. 23.

When the pusher 308 is further pushed into the inner cavity 320 as shown in FIG. 22, the supports 346 of the push rods 344a, 344b are further pushed into the holder hole 322, and the arms 350a, 350b held in abutment with the fulcrum members 330a, 330b further turn about the second pins 354, pulling the hub holder 304 further toward the pusher 308 in the direction indicated by the arrow X2. When the end of the pusher 308 abuts against the step at the boundary between the inner cavity 320 and the holder hole 322, the pusher 308 reaches the end of its stroke. The puncturing process is now finished.

The body 302 of the puncture instrument 300 is of a hollow cylindrical shape. Before the puncture instrument 300 is in use, the front end portion 302a of the body 302 with the protective cap 312 mounted thereon is highly sealed. Specifically, the needle passage 316 in which the needle 40 is housed is highly hermetically sealed to keep the needle 40 sterilized after the needle 40 has been sterilized.

In the illustrated present embodiment, the hub 306 and the hub holder 304 are separate from each other. However, the hub 306 and the hub holder 304 may be integrally combined with each other.

A puncture instrument 400 according to a fifth embodiment of the present invention will be described below with reference to FIGS. 23 to 28. Those parts of the puncture instrument 400 which are identical to those of the puncture instruments 10, 100, 200, 400 according to the first, second, third, and fourth embodiments are denoted by identical reference characters, and will not be described in detail below.

As shown in FIGS. 23 to 28, the puncture instrument 400 comprises a body 402, a movable member (pusher) 404 displaceably disposed in the body 402, an adjustment dial 406 for adjusting the depth to which the needle 40 on the movable member 404 punctures the skin, and a protective cap 408 mounted on the front end of the body 402.

The body 402 is of a hollow, substantially cylindrical structure and has a small-diameter portion 410 on its front end in which the needle 40 is inserted and a large-diameter portion 412 on its rear end that is greater in diameter than the small-diameter portion 410. The movable member 404 is partly exposed from the rear end of the body 402. The small-diameter portion 410 and the large-diameter portion 412 are substantially constant in diameter. The small-diameter portion 410 has an externally threaded outer circumferential surface 414.

The body 402 has a needle passage 416 formed axially centrally through the small-diameter portion 410, and an inner cavity 418 formed in the large-diameter portion 412 with the movable member 404 disposed in the inner cavity 418. The body 402 also has a holder hole 420 (hub passage) formed therein axially between the needle passage 416 and the inner cavity 418. The movable member 404 has a base 432 held in the holder hole 420. The small-diameter portion 410 has a cap hole 422 formed therein at the end of the needle passage 416. The protective cap 408 is partly mounted in the cap hole 422. The cap hole 422 is open outwardly at the distal end of the small-diameter portion 410 and is larger in diameter than the needle passage 416.

The large-diameter portion 412 includes an annular ridge 424 disposed on the proximal end of the inner cavity 418 and slightly projecting radially inwardly. The movable member 404 has an outer circumferential surface slidably engaging the annular ridge 424.

The holder hole 420 is of a substantially rectangular cross-sectional shape. A pair of fulcrum members 426a, 426b is disposed on the inner wall surface of holder hole 420 in alignment with the axis of the body 402. The fulcrum members 426a, 426b extend rearward a predetermined distance from the inner wall surface on the needle passage 416 side and have ends of a semicircular cross-sectional shape. A pair of guide slots 428 is formed in the inner wall surface of holder hole 420 at respective positions that are angularly spaced from the fulcrum members 426a, 426b by 90°. The guide slots 428 extend in the axial direction of the body 402 in the directions indicated by the arrows X1, X2.

The movable member 404 comprises a needle assembly 430 including a needle 40 and a hub 429 which holds the needle 40, a base 432 on which the needle assembly 430 is mounted, a pair of arms 434a, 434b integrally joined to the base 432, a pair of push rods 436a, 436b integrally joined to the respective arms 434a, 434b, and a pusher button 438 for pushing the push rods 436a, 436b forwardly.

The arms 434a, 434b include respective first junctions 440 at one ends joined to the base 432 and respective second junctions 442 at the other ends joined to the distal ends of the push rods 436a, 436b. In the state ready for puncture, the arms 434a, 434b are inclined at a certain angle to the axis of the movable member 404 and are disposed in a mutually crossing relation to each other with the base 432 therebetween as shown in FIG. 25.

The arms 434a, 434b have respective recesses 444 formed in rear surfaces thereof at the first junctions 440, and respective recesses 446 formed in front surfaces thereof at the second junctions 442. Therefore, the first junctions 440 and the second junctions 442 are narrower than the rest of the arms 434a, 434b.

The push rods 436a, 436b project from the end face of the button 438 and extend in the axial direction of the movable member 404. The second junctions 442 of the arms 434a, 434a are connected respectively to the distal ends of the push rods 436a, 436b.

Figure 25:
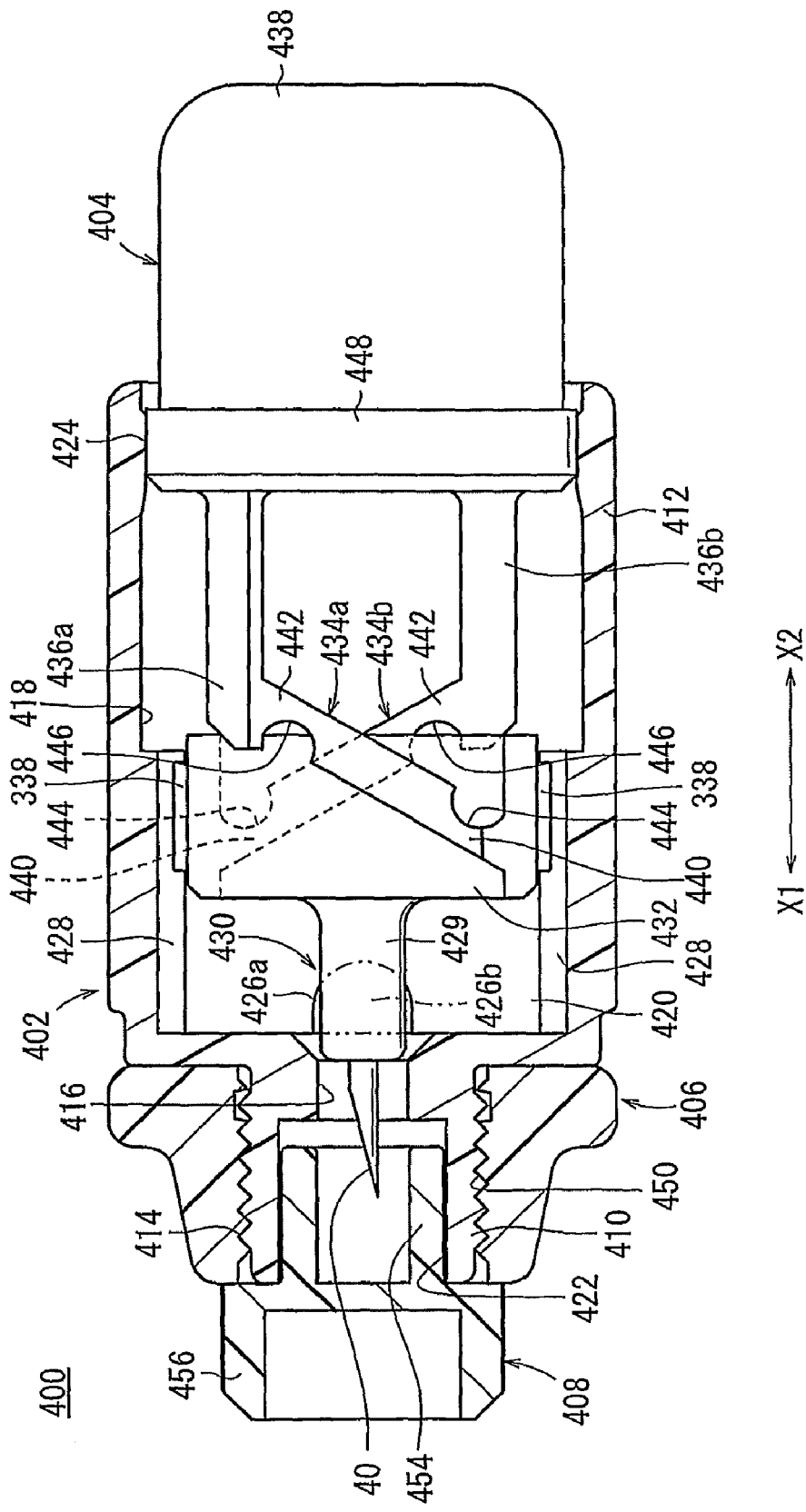
FIG. 25 is a cross-sectional view of the puncture instrument shown in FIG. 23, showing the puncture instrument in a state ready for puncture.

The button 438 is disposed to close the opening of the inner cavity 418, and has its end projecting from the inner cavity 418 when the puncture instrument 400 is in the state ready for puncture (see FIG. 25). The other end of button 438 to which the push rods 436a, 436b are connected has an annular ridge 448 on its outer circumferential surface. When the annular ridge 448 is fitted against the annular ridge 424 formed in the inner cavity 418, the movable member 404 including the button 438 is limited against axial displacement, keeping the inner space including the needle 40 sterilized prior to use.

The adjustment dial 406 is of a ring shape and includes an internally threaded inner circumferential surface 450 threaded over the small-diameter portion 410 of the body 402. The adjustment dial 406 has graduations 452 on its outer circumferential surface. When the adjustment dial 406 is turned, it is axially moved on the small-diameter portion 410 in the directions indicated by the arrows X1, X2. Since the front end of the adjustment dial 406 can be displaced a predetermined distance toward the distal end with respect to the front end of the body 402, it is possible to adjust the distance by which the needle 40 projects from the front end of the adjustment dial 406.

The protective cap 408 comprises a tubular member 454 fitted in the cap hole 422 in the body 402 and a grip 456 joined to the tubular member 454 for being gripped when the protective cap 408 is to be removed. The tubular member 454 is in the form of a hollow bottomed cylinder and houses a portion of the needle 40 therein when the protective cap 408 is mounted on the body 402. In the state that the protective cap 408 is mounted on the body 402, the puncture instrument 400 is irradiated with γ-rays, electron beams, or the like to sterilize the needle 40 in the tubular member 454.

The puncture instrument 400 operates as follows: In the state ready for puncture as shown in FIG. 25, the grip 456 of the protective cap 408 is twisted to release the tubular member 454 out of fitting engagement with the body 402, thereby removing the protective cap 408.

Then, the body 402 is held by hand to abut the front end portion on the skin (not shown), and the button 438 of the movable member 404 is pushed toward the body 402 in the direction indicated by the arrow X1. The annular ridge 448 of the button 438 is out of engagement with the annular ridge 424 of the body 402 and inserted into the inner cavity 418. The movable member 404 is now guided toward the front end portion of the body 402 in the axial direction thereof indicated by the arrow X1 (see FIG. 26).

Figure 26:
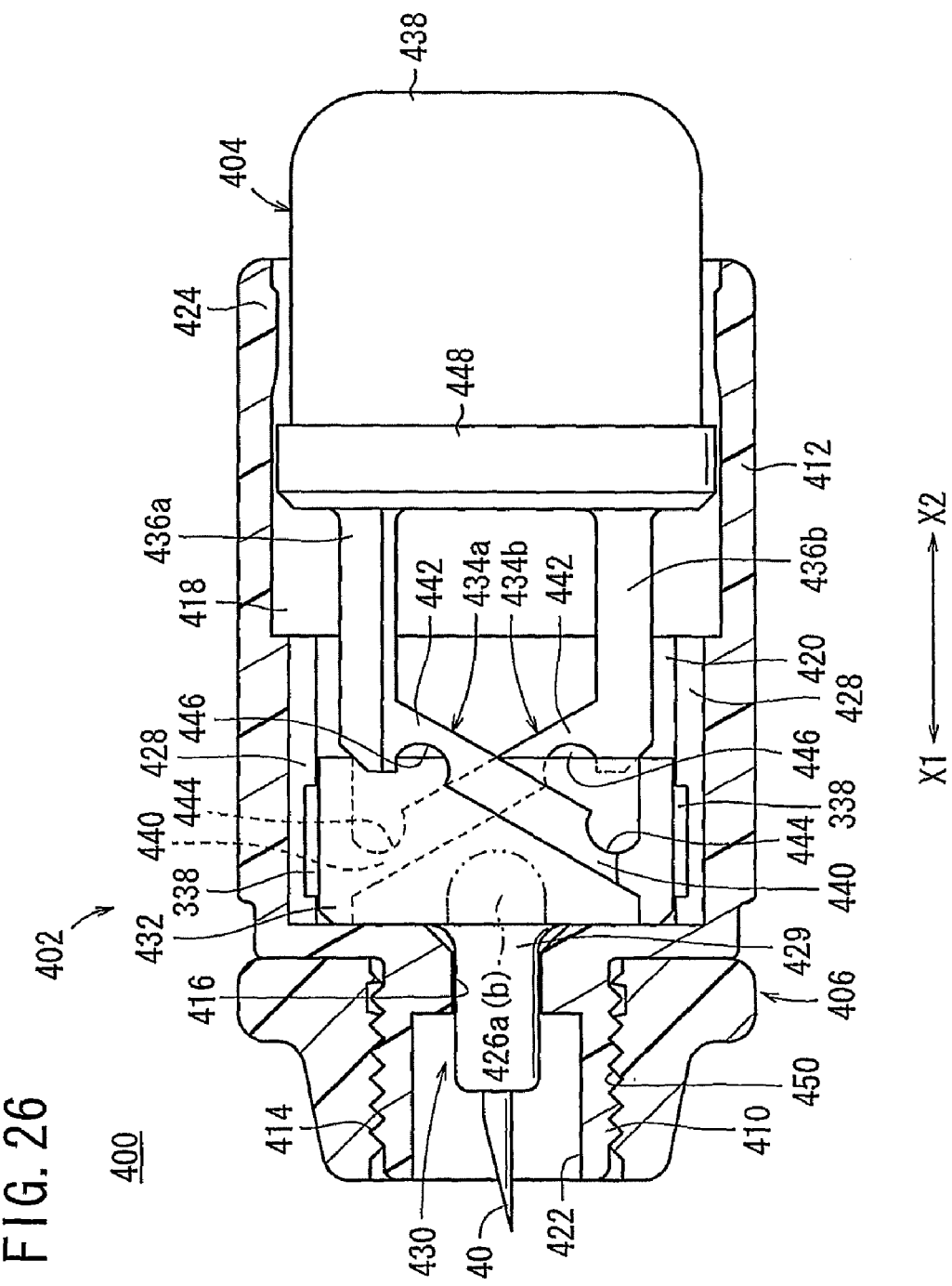
FIG. 26 is a cross-sectional view of the puncture instrument shown in FIG. 23, showing the manner in which after a protective cap is removed from the puncture instrument a needle punctures the skin.

As shown in FIG. 26, as the movable member 404 is displaced toward the front end portion of the body 402 in the direction indicated by the arrow X1, the hub 429 mounted on the base 432 is displaced in and along the needle passage 416 and the cap hole 422. At this time, the movable member 404 is displaced only axially without being rotated about its own axis because it is guided by the guide rails 338 engaging in the respective guide slots 428.

The tip end of the needle 40 projects from the front end portion of the body 402 and punctures the skin. Specifically, the needle 40 is not biased axially by an elastic body, but is pushed directly by the push rods 436a, 346b and the arms 434a, 434b as the movable member 404 is pushed. The wall surface of the holder hole 420 limits the axial displacement of the needle 40 by abutment against the base 432.

Figure 27:
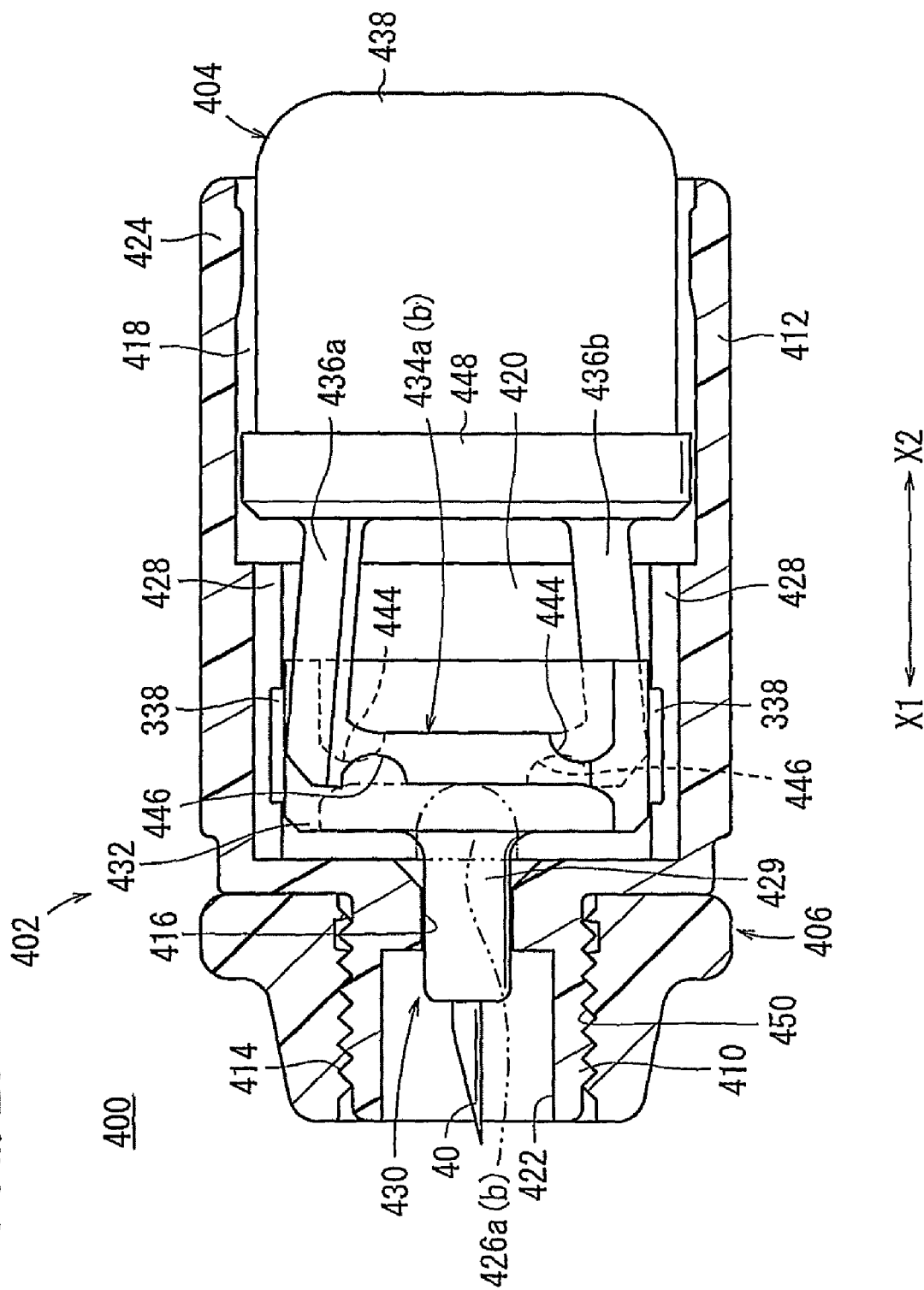
FIG. 27 is a cross-sectional view of the puncture instrument shown in FIG. 23 with arms abutted against fulcrum members and turning.

As shown in FIG. 27, when the pusher 404 is further pushed in, the substantially central regions of the arms 434a, 434b abut against the fulcrum members 426a, 426b, and the arms 434a, 434b gradually turn about the abutting regions so as to move the first junctions 440 toward the proximal end of the body 402 and the second junctions 442 toward the distal end of the body 402. As the arms 434a, 434b turn, the base 432 is pulled toward the button 438 in the direction indicated by the arrow X2, displacing the hub 429 held by the base 432 into the body 402 thereby to retract the needle 40 into the needle passage 416 of the body 402. At this time, the distal ends of the push rods 436a, 436b are elastically bent outwardly away from each other.

Figure 28:
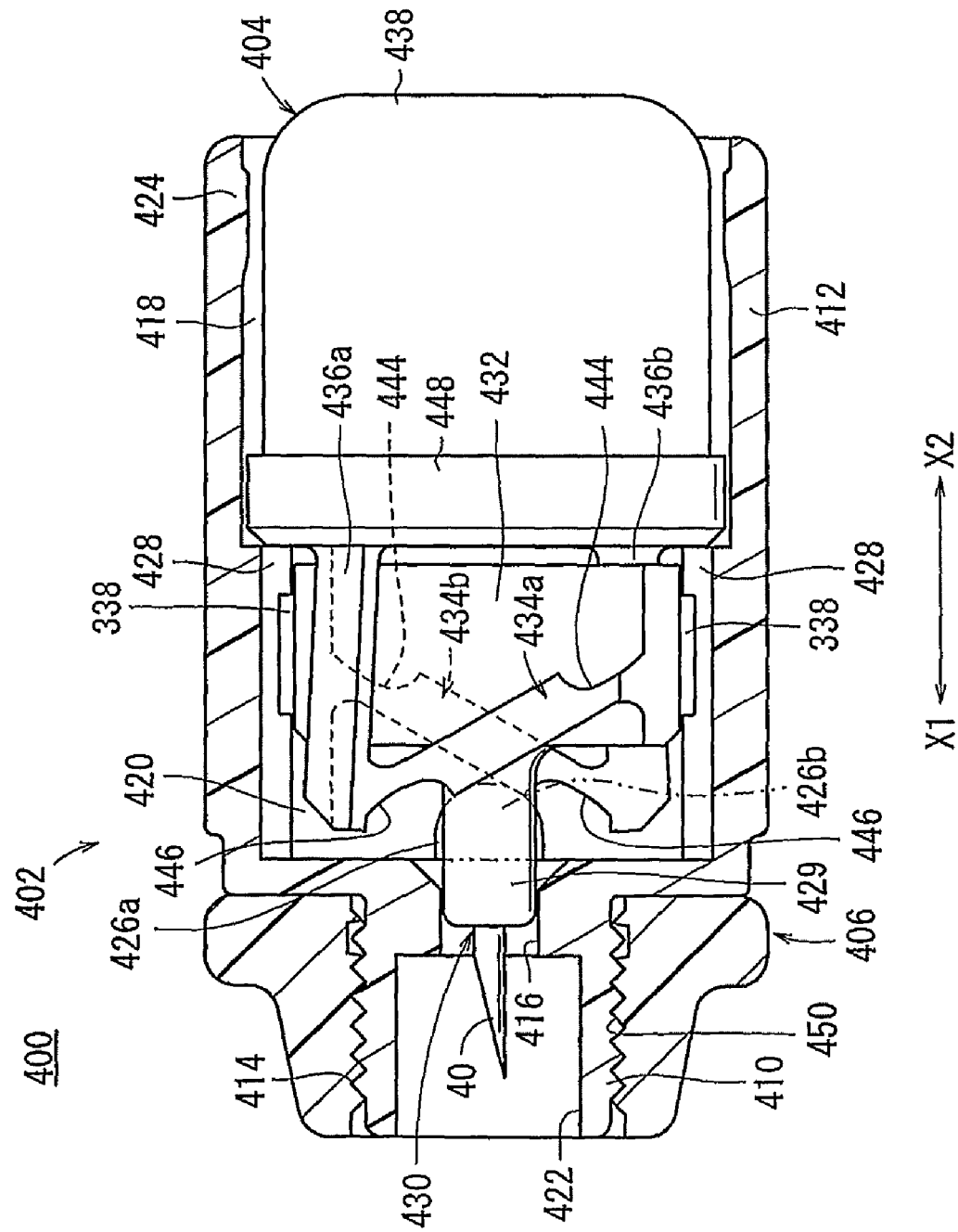
FIG. 28 is a cross-sectional view of the puncture instrument shown in FIG. 23 at the time a movable member has reached the end of its stroke.

When the movable member 404 is further pushed into the inner cavity 418 as shown in FIG. 28, the second junctions 442 of the arms 434a, 434b are pushed in toward the front end portion of the body 402 by the push rods 436a, 436b, and the first junctions 440 of the arms 434a, 434b are pulled toward the button 438 in the direction indicated by the arrow X2, which is opposite to the direction in which the second junctions 442 are pushed, because the arms 434a, 434b are abutted against the fulcrum members 426a, 426b. The base 432 is further moved toward the button 438 in the direction indicated by the arrow X2, moving the hub 429 and the needle 40 along the needle passage 416 toward the button 438.

When the end of the button 438 abuts against the step at the boundary between the inner cavity 418 and the holder hole 420, the button 438 reaches the end of its stroke. The puncturing process is now finished.

Since the annular ridge 448 of the button 438 is fully inserted in the inner cavity 418, the button 438 will not inadvertently be brought out of the inner cavity 418 beyond the annular ridge 424 after the puncturing process is finished. If a second annular ridge is provided on the inner circumferential surface of the inner cavity 418 near the holder hole 420 for engagement with the annular ridge 448, then the button 438 is prevented more effectively from being brought out of the inner cavity 418.

As the body 402 is of a hollow, substantially cylindrical structure, the front end portion of the body 402 on which the protective cap 408 is mounted and the rear end portion of the body 402 in which the button 438 is fitted are highly sealed before the puncture instrument 400 is used. As a result, the needle 40 remains sterilized after sterilization.

The arms 434a, 434b are constituted as integral components of the movable member 404, unlike the arms of the puncture instrument 300 according to the fourth embodiment. Therefore, the puncture instrument 400 is made of a reduced number of components and can be assembled with a reduced number of assembling steps.

Although certain preferred embodiments of the present invention have been shown and described in detail, it should be understood that various changes and modifications may be made therein without departing from the scope of the appended claims.

The invention claimed is:

1. A puncture instrument comprising:
a case;
a needle assembly movably disposed in the case and including a needle and a hub holding the needle;
a hub passage for axially guiding the hub, the hub passage being disposed in the case;
a needle passage disposed in the case and communicating with the hub passage, the needle passage having a distal end opening for allowing a tip end of the needle to project therethrough;
at least one arm having a first junction on an end thereof connected to the hub and a second junction on another end thereof, the arm being inclined from the first junction toward a proximal end of the case in an initial state;
a push rod joined to the second junction and extending toward the proximal end;
a pusher for pushing the push rod toward a distal end of the case; and
a fulcrum member separate from the arm in the initial state and abutting against a portion of the arm when the arm moves;
wherein when the push rod is pushed toward the distal end by the pusher, the arm pushes the needle assembly toward the distal end, brings the portion thereof into abutment with the fulcrum member, and turns about the fulcrum member, so that the arm is inclined from the first junction toward the distal end thereby to pull back the needle assembly toward the proximal end.

2. A puncture instrument according to claim 1, wherein the push rod comprises a leaf spring which is elastically deformable under force applied from the arm when the push rod is pushed toward the distal end by the pusher.

3. A puncture instrument according to claim 1, wherein the arm is inclined toward the proximal end in a direction away from the hub in the initial state, and when the push rod is pushed toward the distal end as the pusher is pushed, the arm turns about the fulcrum member and inclined toward the distal end in a direction away from the hub.

4. A puncture instrument according to claim 1, wherein at least one of the first junction and the second junction is narrower than the arm and is plastically deformable when the arm turns and changes its inclination direction.

5. A puncture instrument according to claim 1, wherein the hub includes a base on a proximal end portion thereof and having a flat surface parallel to a plane in which the arm turns, the first junction being rotatably connected to the base at a position which is spaced a predetermined distance from a longitudinal axis of the hub.

6. A puncture instrument according to claim 1, wherein the pusher includes a convex or concave engaging portion, and the case includes a first engageable portion for engaging the engaging portion when the pusher is in an initial position and a second engageable portion for engaging the engaging portion when the pusher is in a stroke end position.

7. A puncture instrument according to claim 6, wherein the pusher is movably disposed in an inner cavity formed in the case and has a proximal end projecting from the case by a distance ranging from 5 to 30 mm when the pusher is in an initial position, and projecting from the case by a distance of less than 5 mm when the pusher is in a stroke end position.

8. A puncture instrument according to claim 1, wherein the needle passage is narrower than the hub passage, and a step is provided between the needle passage and the hub passage, for abutting a distal end surface of the hub on the step to limit the needle assembly against movement.

9. A puncture instrument according to claim 1, wherein the arm comprises two arms and the push rod comprises two push rods, the two arms and the two push rods being symmetrical about a longitudinal axis of the hub.

10. A puncture instrument according to claim 1, further comprising:
biasing means for biasing the pusher to be pushed toward the distal end; and a stopper for limiting the pusher biased by the biasing means against movement toward the distal end and releasing the pusher in response to operation of a trigger.

11. A puncture instrument according to claim 1, wherein the case is of a hollow cylindrical shape, further comprising:
a protective cap removably mounted on the distal end of the case for holding and sealing the needle in the needle passage.

12. A puncture instrument comprising:
a case;
a needle assembly movably disposed in the case and including a needle and a hub holding the needle;
a hub passage for axially guiding the hub, the hub passage being disposed in the case;
a needle passage disposed in the case and communicating with the hub passage, the needle passage having a distal end opening for allowing a tip end of the needle to project therethrough;
at least one arm having a first junction on an end thereof connected to the hub and a second junction on another end thereof, the arm being inclined from the first junction toward a proximal end of the case in an initial state;
a push rod joined to the second junction and extending toward the proximal end;
a pusher for pushing the push rod toward a distal end of the case; and
a fulcrum member positioned distally of the first junction in the initial state and abutting against a portion of the arm when the arm moves;
wherein when the push rod is pushed toward the distal end by the pusher, the arm pushes the needle assembly toward the distal end, brings the portion thereof into abutment with the fulcrum member, and turns about the fulcrum member, so that the arm is inclined from the first junction toward the distal end thereby to pull back the needle assembly toward the proximal end.

13. A puncture instrument according to claim 12, wherein the at least one arm comprises two arms spaced apart from one another on opposite sides of a longitudinal axis of the hub and each connected to the hub at a respective first junction located at one end of the arm and each possessing a respective second junction at an opposite end of the arm, each of the arms being inclined in the initial state so that the first junction of each arm is positioned distally of the second junction of the respective arm, the fulcrum member abutting against a portion of each arm when the arms move from the initial state toward the fulcrum in response to pushing of the push rod to turn each arm about the fulcrum and cause the second junction of each arm to be positioned distally of the first junction of the respective arm.

14. A puncture instrument according to claim 12, wherein the arm is inclined toward the proximal end in a direction away from the hub in the initial state, and when the push rod is pushed toward the distal end as the pusher is pushed, the arm turns about the fulcrum member and changes inclination so that the arm is inclined toward the distal end in a direction away from the hub.

15. A puncture instrument according to claim 12, wherein at least one of the first junction and the second junction is narrower than the arm and is plastically deformable when the arm turns and changes its inclination direction.

16. A puncture instrument according to claim 12, wherein the hub includes a base on a proximal end portion of the hub and having a flat surface parallel to a plane in which the arm turns, the first junction being rotatably connected to the base at a position spaced a predetermined distance from a longitudinal axis of the hub.

17. A puncture instrument according to claim 12, wherein the pusher includes a convex or concave engaging portion, and the case includes a first engageable portion configured to engage the engaging portion when the pusher is in an initial position and a second engageable portion configured to engage the engaging portion when the pusher is in a stroke end position.

18. A puncture instrument according to claim 12, wherein the needle passage is narrower than the hub passage, and a step is provided between the needle passage and the hub passage, for abutting a distal end surface of the hub on the step to limit the needle assembly against movement.

19. A puncture instrument according to claim 12, wherein the at least one arm comprises two spaced apart arms each connected to the hub at respective first junctions spaced apart from one another.

20. A puncture instrument comprising:
a case;
a needle assembly movably disposed in the case and including a needle and a hub holding the needle;
a hub passage for axially guiding the hub, the hub passage being disposed in the case;
a needle passage disposed in the case and communicating with the hub passage, the needle passage having a distal end opening for allowing a tip end of the needle to project therethrough;
at least one arm connected to the hub at a first junction located at one end of the at least one arm, the at least one arm also including a second junction on an opposite end of the at least one arm, the arm being inclined from the first junction toward a proximal end of the case in an initial state so that the first junction is positioned distally of the second junction;
a push rod joined to the second junction and extending toward the proximal end;
a pusher for pushing the push rod toward a distal end of the case;
a fulcrum member for abutting against a portion of the arm when the arm moves; and
the push rod being movable toward the distal end by the pusher to cause the arm to push the needle assembly toward the distal end, to bring the portion of the arm into abutment with the fulcrum member and turn the arm about the fulcrum member so the arm is inclined from the first junction toward the distal end such that the second junction is positioned distally of the first junction to thereby pull back the needle assembly toward the proximal end.

* * * * *